United States Patent
Holland et al.

(10) Patent No.: US 10,611,923 B2
(45) Date of Patent: *Apr. 7, 2020

(54) AZETIDINIUM-CONTAINING COPOLYMERS AND USES THEREOF

(71) Applicant: Novartis AG, Basel (CH)

(72) Inventors: Troy Vernon Holland, Suwanee, GA (US); Frank Chang, Cumming, GA (US); Yongxing Qiu, Suwanee, GA (US); John Dallas Pruitt, Suwanee, GA (US); Chung-Yuan Chiang, Johns Creek, GA (US); Venkat Shankar, Suwanee, GA (US); Robert Scott, Rancho Santa Margarita, CA (US); Yash Kapoor, North Wales, PA (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/057,867

(22) Filed: Aug. 8, 2018

(65) Prior Publication Data

US 2018/0346753 A1    Dec. 6, 2018

Related U.S. Application Data

(62) Division of application No. 15/216,125, filed on Jul. 21, 2016, now Pat. No. 10,100,219, which is a division of application No. 13/913,734, filed on Jun. 10, 2013, now Pat. No. 9,422,447.

(60) Provisional application No. 61/659,592, filed on Jun. 14, 2012.

(51) Int. Cl.
| | | |
|---|---|---|
| C09D 133/24 | (2006.01) | |
| C09D 139/04 | (2006.01) | |
| C08F 283/12 | (2006.01) | |
| C07D 205/04 | (2006.01) | |
| C08F 220/54 | (2006.01) | |
| C08F 220/56 | (2006.01) | |
| C08F 224/00 | (2006.01) | |
| C08F 20/00 | (2006.01) | |
| C09D 133/26 | (2006.01) | |
| C09D 137/00 | (2006.01) | |
| B29D 11/00 | (2006.01) | |
| C08F 26/00 | (2006.01) | |
| C09D 151/08 | (2006.01) | |

(52) U.S. Cl.
CPC ...... *C09D 133/24* (2013.01); *B29D 11/00865* (2013.01); *C07D 205/04* (2013.01); *C08F 20/00* (2013.01); *C08F 26/00* (2013.01); *C08F 220/54* (2013.01); *C08F 220/56* (2013.01); *C08F 224/00* (2013.01); *C08F 283/124* (2013.01); *C09D 133/26* (2013.01); *C09D 137/00* (2013.01); *C09D 139/04* (2013.01); *C09D 151/085* (2013.01); *C08F 2500/26* (2013.01)

(58) Field of Classification Search
None
See application file for complete search history.

(56) References Cited

PUBLICATIONS

Bogaert et al., Reactive Polymers Containing Pendant Azetidine or Azetinium Functions, 1 Synthesis of Poly(acrylic ester)s and Poly(methacrylic ester)s of 1-Alkyl-3-hydroxyazetidines and Related Azetidinium Salts. Makromol. Chem. 1981, 182, 2687-2693.*

* cited by examiner

*Primary Examiner* — Po-Chih Chen
(74) *Attorney, Agent, or Firm* — Jian Zhou

(57) ABSTRACT

The invention is related to azetidinium-containing copolymers and vinylic monomers and their uses in formation of non-silicone hydrogel coatings on silicone hydrogel contact lenses.

16 Claims, 1 Drawing Sheet

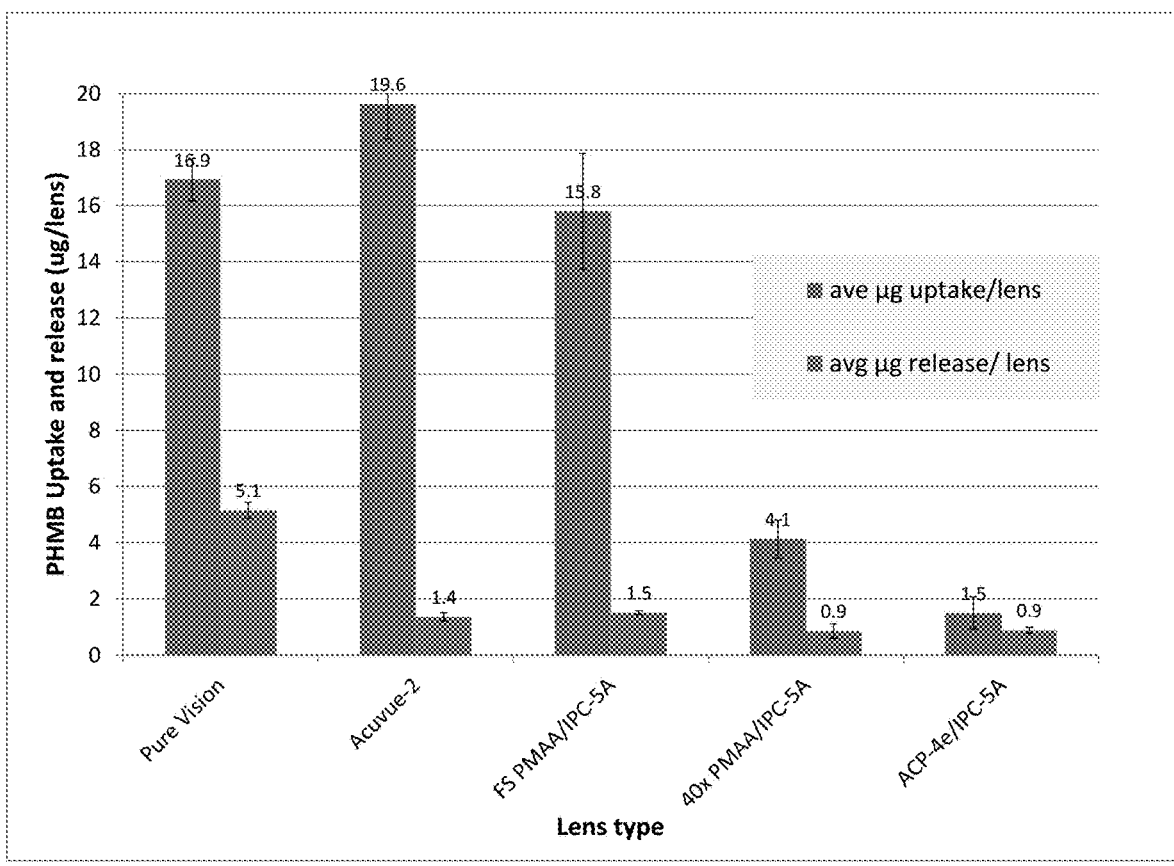

AZETIDINIUM-CONTAINING COPOLYMERS AND USES THEREOF

This application is a division of application Ser. No. 15/216,125 filed 21 Jul. 2016, which is a division of application Ser. No. 13/913,734 filed 10 Jun. 2013, now U.S. Pat. No. 9,422,447, which claims the benefits under 35 USC § 119 (e) of U.S. provisional application No. 61/659,592 filed 14 Jun. 2012, incorporated by reference in its entirety.

The present invention generally relates to azetidinium-containing vinylic monomers and copolymers suitable for applying a hydrogel coating onto a silicone hydrogel contact lens in a cost-effective and time-efficient manner. In addition, the present invention provides an ophthalmic lens product.

BACKGROUND

Soft silicone hydrogel contact lenses are increasingly becoming popular because of their high oxygen permeability and comfort. But, a silicone hydrogel material typically has a surface, or at least some areas of its surface, which is hydrophobic (non-wettable) and susceptible to adsorbing lipids or proteins from the ocular environment and may adhere to the eye. Thus, a silicone hydrogel contact lens will generally require a surface modification.

A known approach for modifying the hydrophilicity of a relatively hydrophobic contact lens material is through the use of a plasma treatment, for example, commercial lenses such as Focus NIGHT & DAY™ and O2OPTIX™ (CIBA VISION), and PUREVISION™ (Bausch & Lomb) utilize this approach in their production processes. Advantages of a plasma coating, such as, e.g., those may be found with Focus NIGHT & DAY™, are its durability, relatively high hydrophilicity/wettability), and low susceptibility to lipid and protein deposition and adsorption. But, plasma treatment of silicone hydrogel contact lenses may not be cost effective, because the preformed contact lenses must typically be dried before plasma treatment and because of relative high capital investment associated with plasma treatment equipment.

Various other approaches are proposed and/or used for modifying the surface hydrophilicity of a silicone hydrogel contact lens. Examples of such other approaches include incorporation of wetting agents (hydrophilic polymers) into a lens formulation for making the silicone hydrogel contact lens (see, e.g., U.S. Pat. Nos. 6,367,929, 6,822,016, 7,052,131, and 7,249,848); a layer-by-layer (LbL) polyionic material deposition technique (see, e.g., U.S. Pat. Nos. 6,451,871; 6,719,929; 6,793,973; 6,884,457; 6,896,926; 6,926,965; 6,940,580; and 7,297,725, and U.S. Pat. Appl. Pub. Nos. 2007/0229758A1; 2008/0174035A1 and 2008/0152800A1); crosslinking of LbL coatings on contact lenses has been proposed in commonly-owned copending US pat. Appl. pub. Nos. 2008/0226922 A1 and 2009/0186229 A1; and attachment of hydrophilic polymers onto contact lenses according to various mechanisms (see for example, U.S. Pat. Nos. 6,099,122, 6,436,481, 6,440,571, 6,447,920, 6,465,056, 6,521,352, 6,586,038, 6,623,747, 6,730,366, 6,734,321, 6,835,410, 6,878,399, 6,923,978, 6,440,571, and 6,500,481, US Pat. Appl. Pub. Nos. 2009/0145086A1, 2009/0145091A1, 2008/0142038A1, and 2007/0122540A1). Although those techniques can be used in rendering a silicone hydrogel material wettable, there are some shortcomings in those techniques. For example, wetting agents may impart haziness to the resultant lenses because of their incompatibility with other silicone components in the lens formulation and may not provide a durable hydrophilic surface for extended wear purposes. LbL coatings may not be as durable as plasma coatings and may have relatively high densities of surface charges; which may interfere with contact lens cleaning and disinfecting solutions. Crosslinked LbL coatings may have a hydrophilicity and/or wettability inferior than original LbL coatings (prior to crosslinking) and still have relative high densities of surface charges. In addition, they may not be cost-effective and/or time-efficient for implementation in a mass production environment, because they typically require relatively long time and/or involve laborious, multiple steps to obtain a hydrophilic coating.

Recently, a new cost-effective approach has been described in U.S. pat. Appl. pub. No. 2012/0026457 A1 (herein incorporated by reference in its entirety) for applying a non-silicone hydrogel coating onto a silicone hydrogel contact lens. It is reported in the publication that a partially-crosslinked hydrophilic polymeric material derived from a polyamidoamine epichlorohydrin (PAE) and a wetting agent are used in the formation of non-silicone hydrogel coating on a contact lens. Although this new approach can provide silicone hydrogel contact lenses with durable hydrophilic coatings thereon, its applicability and advantages can be limited by the lack of versatility and controllability in the levels of hydrophilicity and/or reactive functional group contents of the partially-crosslinked hydrophilic polymeric material.

Therefore, there is still a need for reactive copolymers having desired level of hydrophilicity and/or functional groups content for applying a non-silicone hydrogel coating onto a silicone hydrogel contact lens.

SUMMARY OF THE INVENTION

The invention, in the first aspect, provides an azetidinium-containing vinylic monomer.

The invention, in the second aspect, provides an azetidinium-containing copolymer comprising azetidinium-containing monomeric units derived from at least one azetidinium-containing vinylic monomer of the invention and monomeric units derived from at least one vinylic monomer selected from the group consisting of a carboxyl-containing vinylic monomer, an amino-containing vinylic monomer, a hydrophobic vinylic monomer, and combination thereof.

The invention, in the third aspect, provides a method for producing coated silicone hydrogel contact lenses each having a crosslinked hydrophilic coating thereon, the method of invention comprising the steps of: (a) obtaining a silicone hydrogel contact lens; (b) applying a prime coating of an anchoring polymer onto the silicone hydrogel contact lens, wherein the anchoring polymer is a homopolymer or copolymer of a carboxyl-containing vinylic monomer and/or an azetidinium-containing copolymer of the invention; and (c) heating the silicone hydrogel contact lens in an aqueous solution in the presence of a water-soluble thermally-crosslinkable hydrophilic polymeric material comprising azetidinium, carboxyl, amino, and/or thiol groups, to and at a temperature from about 40° C. to about 140° C. for a period of time sufficient to induce intermolecular and intramolecular crosslinking reactions between one azetidinium group and one amino or carboxyl group, thereby forming a durable non-silicone hydrogel coating on the silicone hydrogel contact lens, provided that at least one of the anchoring polymer and the water-soluble thermally-crosslinkable hydrophilic polymeric material comprises azetidinium groups.

The invention, in the fourth aspect, provides a method for producing silicone hydrogel contact lenses each having a crosslinked hydrophilic coating thereon, the method of invention comprising the steps of: (a) obtaining a silicone hydrogel contact lens from a lens-forming composition comprising an azetidinium-containing copolymer of the invention; (b) heating the silicone hydrogel contact lens in an aqueous solution in the presence of a water-soluble, thermally-crosslinkable hydrophilic polymeric material comprising azetidinium, carboxyl, amino, and/or thiol groups, to and at a temperature from about 40° C. to about 140° C. for a period of time sufficient to induce intermolecular and intramolecular crosslinking reactions between one azetidinium group and one amino or carboxyl group, thereby forming a durable non-silicone hydrogel coating on the silicone hydrogel contact lens.

In the fifth aspect, the invention provides a silicone hydrogel contact lens comprising a non-silicone hydrogel coating thereon, wherein the non-silicone hydrogel coating is obtained by thermally inducing intermolecular and intramolecular crosslinking of a thermally-crosslinkable hydrophilic polymeric material which comprises azetidinium-containing monomeric units derived from at least one azetidinium-containing vinylic monomer, reactive monomeric units derived from a vinylic monomer having an amino or carboxyl group, and hydrophilic monomeric units derived from a hydrophilic vinylic monomer, wherein the silicone hydrogel contact lens has an oxygen permeability of at least about 40 barrers, a surface wettability characterized by a water contact angle of about 100 degrees or less, and a good coating durability characterized by surviving a digital rubbing test.

In the sixth aspect, the invention provides an ophthalmic product, which comprises a sterilized and sealed lens package, wherein the lens package comprises: a post-autoclave lens packaging solution and a readily-usable silicone hydrogel contact lens immersed therein, wherein the readily-usable silicone hydrogel contact lens comprises a crosslinked hydrophilic coating obtained by autoclaving an original silicone hydrogel contact lens having amino groups and/or carboxyl groups on and/or near the surface of the original silicone hydrogel contact lens in a pre-autoclave packaging solution containing a water-soluble and thermally-crosslinkable hydrophilic polymeric material which comprises from 0.001% to about 25% by mole of azetidinium-containing monomeric units derived from at least one azetidinium-containing vinylic monomer, wherein the hydrophilic polymeric material is covalently attached onto the silicone hydrogel contact lens through second covalent linkages each formed between one amino or carboxyl group on and/or near the surface of the silicone hydrogel contact lens and one azetidinium group of the hydrophilic polymeric material, wherein the post-autoclave packaging solution comprises at least one buffering agent in an amount sufficient to maintain a pH of from about 6.0 to about 8.5 and an hydrolyzed product of the hydrophilic polymeric material and has a tonicity of from about 200 to about 450 milliosmol (mOsm) and a viscosity of from about 1 centipoise to about 10 centipoises.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

BRIEF DESCRIPTION OF THE DRAWINGS

FIG. 1 shows polyhexamethylene biguanide (PHMB) uptakes and releases by various contact lenses.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art. Also, as used in the specification including the appended claims, reference to singular forms such as "a," "an," and "the" include the plural, and reference to a particular numerical value includes at least that particular value, unless the context clearly dictates otherwise. "About" as used herein means that a number referred to as "about" comprises the recited number plus or minus 1-10% of that recited number.

A "silicone hydrogel contact lens" refers to a contact lens comprising a silicone hydrogel material. A "silicone hydrogel" refers to a crosslinked silicone-containing polymeric material which can absorb at least 10 percent by weight of water when it is fully hydrated and is obtained by copolymerization of a polymerizable composition comprising at least one silicone-containing vinylic monomer or at least one silicone-containing vinylic macromer or at least one silicone-containing prepolymer having ethylenically unsaturated groups.

As used in this application, the term "hydrogel" or "hydrogel material" refers to a crosslinked polymeric material which is not water-soluble and can contains at least 10% by weight of water within its polymer matrix when fully hydrated.

As used in this application, the term "non-silicone hydrogel" refers to a hydrogel that is theoretically free of silicon.

A "vinylic monomer", as used herein, refers to a compound that has one sole ethylenically unsaturated group and can be polymerized actinically or thermally.

The term "olefinically unsaturated group" or "ethylenically unsaturated group" is employed herein in a broad sense and is intended to encompass any groups containing at least one >C=C<group. Exemplary ethylenically unsaturated groups include without limitation (meth)acryloyl methacryloyl

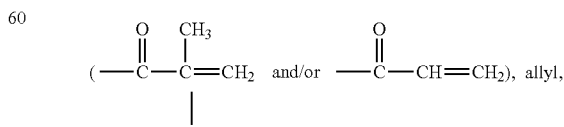

styrenyl, or other C=C containing groups.

The term "(meth)acrylamide" refers to methacrylamide and/or acrylamide.

The term "(meth)acrylate" refers to methacrylate and/or acrylate.

A "hydrophilic vinylic monomer", as used herein, refers to a vinylic monomer which as a homopolymer typically yields a polymer that is water-soluble or can absorb at least 10 percent by weight water.

A "hydrophobic vinylic monomer", as used herein, refers to a vinylic monomer which as a homopolymer typically yields a polymer that is insoluble in water and can absorb less than 10 percent by weight water.

As used in this application, the term "macromer" or "prepolymer" refers to a medium and high molecular weight compound or polymer that contains two or more ethylenically unsaturated groups. Medium and high molecular weight typically means average molecular weights greater than 700 Daltons.

As used in this application, the term "crosslinker" refers to a compound having at least two ethylenically unsaturated groups. A "crosslinking agent" refers to a crosslinker having a molecular weight of about 700 Daltons or less.

As used in this application, the term "polymer" means a material formed by polymerizing/crosslinking one or more monomers or macromers or prepolymers.

As used in this application, the term "molecular weight" of a polymeric material (including monomeric or macromeric materials) refers to the weight-average molecular weight unless otherwise specifically noted or unless testing conditions indicate otherwise.

As used in this application, the term "amino group" refers to a primary or secondary amino group of formula —NHR', where R' is hydrogen or a $C_1$-$C_{20}$ unsubstituted or substituted, linear or branched alkyl group, unless otherwise specifically noted.

The term "carboxyl-containing vinylic monomer" refers to a vinyl monomer having a carboxyl group (—COOH).

The term "amino-containing vinylic monomer" refers to a vinyl monomer having an amino group.

The term "azetidinium" refers to a positively-charged, trivalent radical (or group) of

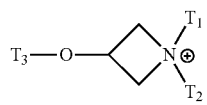

in which $T_1$, $T_2$ and $T_3$ are a direct bond.

The term "phosphorylcholine" refers to a zwitterionic group of

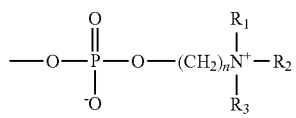

in which n is an integer of 1 to 5 and $R_1$, $R_2$ and $R_3$ independently of each other are $C_1$-$C_8$ alkyl or $C_1$-$C_8$ hydroxyalkyl.

The term "azlactone" refers to a mono-valent radical of

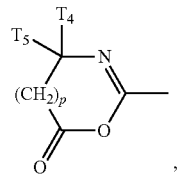

in which p is 0 or 1; $T_4$ and $T_5$ independently of each other is an alkyl group having 1 to 14 carbon atoms, a cycloalkyl group having 3 to 14 carbon atoms, an aryl group having 5 to 12 ring atoms, an arenyl group having 6 to 26 carbon and 0 to 3 sulfur, nitrogen and/or oxygen atoms, or $T_4$ and $T_5$ taken together with the carbon to which they are joined can form a carbocyclic ring containing 5 to 8 ring atoms.

As used in this application, the term "non-reactive hydrophilic vinylic monomer" refers to a hydrophilic vinylic monomer free of carboxyl or amino group.

The term "polysiloxane segment" refers to a bivalent radical having the formula

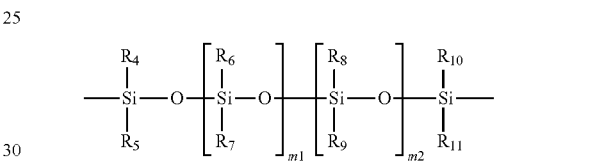

in which $R_4$, $R_5$, $R_6$, $R_7$, $R_8$, $R_9$, $R_{10}$, $R_{11}$, independently of one another, are $C_1$-$C_{10}$ alkyl, $C_1$-$C_4$ alkyl- or $C_1$-$C_4$-alkoxy-substituted phenyl, $C_1$-$C_{10}$ fluoroalkyl, $C_1$-$C_{10}$ fluoroether, $C_6$-$C_{18}$ aryl radical, -alk-$(OC_2H_4)_{n1}$—$OR_9$ in which alk is $C_1$-$C_6$-alkylene divalent radical, $R_9$ is H or $C_1$-$C_4$ alkyl and n1 is an integer from 1 to 10, m1 and m2 independently of each other are an integer of from 0 to 50 and (m1+m2) is from 1 to 100.

The term "water-soluble" in reference to a polymer means that the polymer can be dissolved in water to an extent sufficient to form an aqueous solution of the polymer having a concentration of from about 0.05% to about 30% by weight at room temperature (e.g., from about 22° C. to about 28° C.).

A "water contact angle" refers to an average water contact angle (i.e., contact angles measured by Sessile Drop method), which is obtained by averaging measurements of contact angles with at least 3 individual contact lenses.

The term "intactness" in reference to a coating on a silicone hydrogel contact lens is intended to describe the extent to which the contact lens can be stained by Sudan Black in a Sudan Black staining test described in Example 1. Good intactness of the coating on a silicone hydrogel contact lens means that there is practically no Sudan Black staining of the contact lens.

The term "durability" in reference to a coating on a silicone hydrogel contact lens is intended to describe that the coating on the silicone hydrogel contact lens can survive a digital rubbing test.

As used herein, "surviving a digital rubbing test" or "surviving a durability test" in reference to a coating on a contact lens means that after digitally rubbing the lens according to a procedure described in Example 1, water contact angle on the digitally rubbed lens is still about 100 degrees or less, preferably about 90 degrees or less, more preferably about 80 degrees or less, most preferably about 70 degrees or less.

The intrinsic "oxygen permeability", Dk, of a material is the rate at which oxygen will pass through a material. As used in this application, the term "oxygen permeability (Dk)" in reference to a hydrogel (silicone or non-silicone) or a contact lens means a measured oxygen permeability (Dk) which is corrected for the surface resistance to oxygen flux caused by the boundary layer effect according to the procedures described in Example 1 of 2012/0026457 A1 (herein incorporated by reference in its entirety). Oxygen permeability is conventionally expressed in units of barrers, where "barrer" is defined as [(cm$^3$ oxygen)(mm)/(cm$^2$)(sec)(mm Hg)]×10$^{-10}$.

The "oxygen transmissibility", Dk/t, of a lens or material is the rate at which oxygen will pass through a specific lens or material with an average thickness of t [in units of mm] over the area being measured. Oxygen transmissibility is conventionally expressed in units of barrers/mm, where "barrers/mm" is defined as [(cm$^3$ oxygen)/(cm$^2$)(sec)(mm Hg)]×10$^{-9}$.

The "ion permeability" through a lens correlates with the Ionoflux Diffusion Coefficient. The Ionoflux Diffusion Coefficient, D (in units of [mm$^2$/min]), is determined by applying Fick's law as follows:

$$D=-n'/(A \times dc/dx)$$

where n'=rate of ion transport [mol/min]; A=area of lens exposed [mm$^2$]; dc=concentration difference [mol/L]; dx=thickness of lens [mm].

"Ophthalmically compatible", as used herein, refers to a material or surface of a material which may be in intimate contact with the ocular environment for an extended period of time without significantly damaging the ocular environment and without significant user discomfort.

The term "ophthalmically safe" with respect to a packaging solution for sterilizing and storing contact lenses is meant that a contact lens stored in the solution is safe for direct placement on the eye without rinsing after autoclave and that the solution is safe and sufficiently comfortable for daily contact with the eye via a contact lens. An ophthalmically-safe packaging solution after autoclave has a tonicity and a pH that are compatible with the eye and is substantially free of ocularly irritating or ocularly cytotoxic materials according to international ISO standards and U.S. FDA regulations.

An "organic-based solution" refers to a solution which is a homogeneous mixture consisting of an organic-based solvent and one or more solutes dissolved in the organic based solvent. An organic-based coating solution refers to an organic-based solution containing at least one polymeric coating material as a solute in the solution.

An "organic-based solvent" is intended to describe a solvent system which consists of one or more organic solvents and optionally about 40% or less, preferably about 30% or less, more preferably about 20% or less, even more preferably about 10% or less, in particular about 5% or less by weight of water relative to the weight of the solvent system.

The invention is generally related to azetidinium-containing copolymers and their uses in forming a non-silicone hydrogel coating on a silicone hydrogel (SiHy) contact lens. An azetidinium-containing copolymer of the invention can be tailored to have desired degrees of hydrophilicity/hydrophobicity and/or azetidinium contents. Such azetidinium-containing copolymers can be used as an anchoring polymer and/or an reactive hydrophilic polymer for forming a hydrogel coating, according to thermally-induced reaction mechanism involving an azetidnium group as illustrated in Scheme I Scheme I

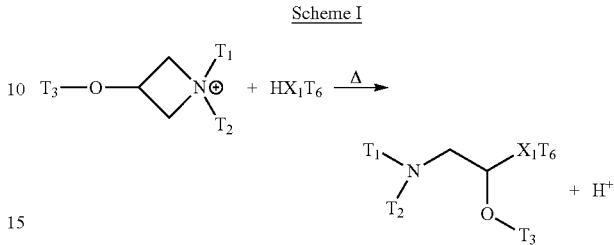

in which $T_1$, $T_2$ and $T_3$ independent of one another are a direct bond; $X_1$ is —S—, —OC(=O)—, —O—, or —NR'— in which R' is hydrogen, a $C_1$-$C_{20}$ unsubstituted or substituted, linear or branched alkyl group; $T_6$ is a polymer chain or a $C_1$ to $C_{20}$ alkyl unsubstituted or substituted, linear or branched alkyl group. Such a reaction can be carried out conveniently and directly in a lens package during autoclave (i.e., heating the lens package with the lens in a packaging solution about 118° C. to about 125° C. for approximately 20-40 minutes under pressure) which is a commonly-used sterilization process in the contact lens industry.

The invention, in one aspect, provides one class of azetidinium-containing vinylic monomers of formula (1)

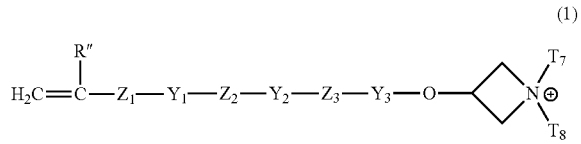

in which: R" is hydrogen or methyl; $T_7$ and $T_8$ independent of each other are $C_1$ to $C_{14}$ alkyl group; $Y_1$, $Y_2$, and $Y_3$ independent of one other are a linkage selected from the group consisting of a direct bond, —O—, —NR'—, —C(O)—NR'—, —NR'—C(O)—, —O—C(O)—NH—, —NH—C(O)—O—, —NR'—C(O)—NH—, —NH—C(O)—NR'—, —C(O)—O—, —O—C(O)—, —NH—C(O)—NH—$Z_0$—NH—C(O)—NH—, —O—C(O)—NH—$Z_0$—NH—C(O)—O—, —O—C(O)—NH—$Z_0$—NH—C(O)—NH—, and —NH—C(O)—NH—$Z_0$—NH—C(O)—O—; R' is hydrogen, a $C_1$-$C_{20}$ unsubstituted or substituted, linear or branched alkyl group; $Z_0$ is a linear or branched $C_2$-$C_{12}$ alkylene divalent radical or a $C_5$-$C_{45}$ cycloaliphatic or aliphatic-cycloaliphatic divalent radical optionally containing therein one or more linkages of —O—, —NR'— and —C(O)—, R' is as defined above; $Z_1$, $Z_2$, and $Z_3$ independent of one other are a direct bond, a $C_1$-$C_{20}$ unsubstituted or substituted, linear or branched alkylene divalent radical optionally containing therein one or more linkages of —O—, —NR'—, and —C(O)—, a $C_1$-$C_7$ alkyleneoxy $C_1$-$C_7$ alkylene divalent radical, a divalent radical of —(CH(R")CH$_2$O)$_{r1}$—CH(R")CH$_2$— in which R" is as defined above and r1 is an integer of 1 to 20, an unsubstituted phenylene divalent radical, $C_1$-$C_4$ alkyl or $C_1$-$C_4$ alkoxy substituted phenylene divalent radical or $C_7$-$C_{12}$ arakylene divalent radical, a $C_5$-$C_{45}$ cycloaliphatic or aliphatic-cycloaliphatic divalent radical optionally containing therein one or more linkages of —O—, —NR'—, and —C(O)—, a $C_6$-$C_{24}$ aromatic or araliphatic divalent radical, or combinations thereof.

An azetidinium-containing vinylic monomer of the invention can be prepared according to a two-step process. In the first step, a di-alkylamine ($HNT_7T_8$) can react with epichlorohydrin

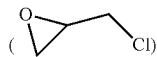

to form an azetidinium compound of

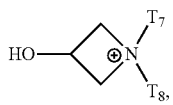

wherein $T_7$ and $T_8$ independent of each other are $C_1$ to $C_{14}$ alkyl group. In the second step, the resultant azetidinium compound reacts, in the absence of a coupling agent, with an ethylenically functionalizing vinylic monomer selected from the group consisting of (meth)acrylic acid halide (chloride, bromide, or iodide), (meth)acrylic anhydride, maleic anhydride, an epoxy-containing vinylic monomer, a $C_2$-$C_6$ isocyanatoalkyl (meth)acrylate, an aziridine-containing vinylic monomer, and an azlactone-containing vinylic monomer, under well-known conditions of coupling reactions between one hydroxyl group and one other functional group (acid halide group, acid anhydride group, epoxy group, isocyanate group, azeridine group, or azlactone group). Alternatively, the resultant azetidinium compound reacts, in the presence of a coupling agent (e.g., a diisocyanate compound, a di-acid halide compound, a di-azlactone compound, or a di-epoxy compound), with an ethylenically functionalizing vinylic monomer selected from the group consisting of $C_2$ to $C_6$ hydroxylalkyl (meth)acrylate, $C_2$ to $C_6$ hydroxyalkyl (meth) acrylamide, allylalcohol, allylamine, amino-$C_2$-$C_6$ alkyl (meth)acrylate, vinylamine, amino-$C_2$-$C_6$ alkyl (meth)acrylamide, acrylic acid, and $C_1$-$C_4$ alkylacrylic acid (e.g., methacrylic ethylacrylic acid, propylacrylic acid, butylacrylic acid), under well-known coupling-reaction conditions.

A "coupling reaction" is intended to describe any reaction between a pair of matching functional groups in the presence or absence of a coupling agent to form covalent bonds or linkages under various reaction conditions well known to a person skilled in the art, such as, for example, oxidation-reduction conditions, dehydration condensation conditions, addition conditions, substitution (or displacement) conditions, Diels-Alder reaction conditions, cationic crosslinking conditions, ring-opening conditions, epoxy hardening conditions, and combinations thereof. Non-limiting examples of coupling reactions under various reaction conditions between a pair of co-reactive functional groups are given below for illustrative purposes. For example, a hydroxyl group reacts with an acid chloride or bromide group or with an acid anhydride group to form an ester linkage (—C(O)—O—); a hydroxyl (or hydroxy) reacts with an isocyanate to form a urethane linkage; a hydroxyl reacts with an epoxy or aziridine to form a OH— or $NH_2$-containing ether linkage (—CH(OH)—$CH_2$—O— or —CH($NH_2$)—$CH_2$—O—); a hydroxyl group reacts with an azlactone group in the presence of a catalyst to form an amidoalkylenecarboxy linkage (—OC(O)—$(CH_2)_p$—$CT_4T_5$-C(O)—NH—); an amino group reacts with aldehyde group to form a Schiff base which may further be reduced; an amino group —NHR' reacts with an acid chloride or bromide group or with an acid anhydride group to form an amide linkage (—CO—NR'—); an amino group —NHR' reacts with an isocyanate group to form a urea linkage (—NR"—C(O)—NH—); an amino group —NHR' reacts with an epoxy or aziridine group to form a OH— or $NH_2$-containing amine bond ((—CH (OH)—$CH_2$—NR'— or —CH($NH_2$)—$CH_2$—NR'—); an amino group —NHR' reacts (ring-opening) with an azlactone group to form an alkylene-diamido linkage (—C(O) NR'—$(CH_2)_p$—$CT_4T_5$-C(O)—NH—); an amino group —NHR' reacts with a carboxylic acid group in the presence of a coupling agent—carbodiimide (e.g., 1-ethyl-3-(3-dimethylaminopropyl) carbodiimide (EDC), N,N'-dicyclohexylcarbodiimide (DCC), 1-cylcohexyl-3-(2-morpholinoethyl) carbodiimide, diisopropyl carbodiimide, or mixtures thereof) to form an amide linkage; a carboxyl group reacts with an epoxy group to form an ester bond.

Any suitable $C_4$-$C_{24}$ diisocyanates can be used in the invention. Examples of preferred diisocyanates include without limitation isophorone diisocyanate, hexamethyl-1, 6-diisocyanate, 4,4'-dicyclohexylmethane diisocyanate, toluene diisocyanate, 4,4'-diphenyl diisocyanate, 4,4'-diphenylmethane diisocyanate, p-phenylene diisocyanate, 1,4-phenylene 4,4'-diphenyl diisocyanate, 1,3-bis-(4,4'-isocyanato methyl) cyclohexane, cyclohexane diisocyanate, and combinations thereof.

Any suitable diacid halides can be used in the invention. Examples of preferred diacid halide include without limitations fumaryl chloride, suberoyl chloride, succinyl chloride, phthaloyl chloride, isophthaloyl chloride, terephthaloyl chloride, sebacoyl chloride, adipoyl chloride, trimethyladipoyl chloride, azelaoyl chloride, dodecanedioic acid chloride, succinic chloride, glutaric chloride, oxalyl chloride, dimer acid chloride, and combinations thereof.

Any suitable di-epoxy compounds can be used in the invention. Examples of preferred di-epoxy compounds are neopentyl glycol diglycidyl ether, 1,4-butanediol diglycidyl ether, 1,6-hexanediol diglycidyl ether, glycerol diglycidyl ether, ethylene glycol diglycidyl ether, diethylene glycol diglycidyl ether, polyethylene glycol diglycidyl ether, propylene glycol diglycidyl ether, dipropylene glycol diglycidyl ether, and combinations thereof. Such di-epoxy compounds are available commercially (e.g., those DENACOL series di-epoxy compounds from Nagase ChemteX Corporation).

Any suitable $C_{10}$-$C_{24}$ di-azlactone compounds can be used in the invention. Examples of such diazlactone compounds are those described in U.S. Pat. No. 4,485,236 (herein incorporated by reference in its entirety).

Preferred examples of aziridine-containing vinylic monomers include without limitation 3-(1-aziridinyl) propyl (meth)acrylate, 4-(1-aziridinyl) butyl (meth)acrylate, 6-(1-aziridinyl) hexyl (meth)acrylate, and 8-(1-aziridinyl) octyl (meth)acrylate.

Preferred examples of epoxy-containing vinylic monomers include without limitation glycidyl (meth)acrylate, vinyl glycidyl ether, and allyl glycidyl ether.

Preferred examples of azlactone-containing vinylic monomers include without limitation 2-vinyl-4,4-dimethyl-1,3-oxazolin-5-one, 2-isopropenyl-4,4-dimethyl-1,3-oxazolin-5-one, 2-vinyl-4-methyl-4-ethyl-1,3-oxazolin-5-one, 2-isopropenyl-4-methyl-4-butyl-1,3-oxazolin-5-one, 2-vinyl-4,4-dibutyl-1,3-oxazolin-5-one, 2-isopropenyl-4-methyl-4-dodecyl-1,3-oxazolin-5-one, 2-isopropenyl-4,4-diphenyl-1,3-oxazolin-5-one, 2-isopropenyl-4,4-pentamethylene-1,3-oxazolin-5-one, 2-isopropenyl-4,4- tetramethylene-1,3-oxazolin-5-one, 2-vinyl-4,4-diethyl-1,3-oxazolin-5-one, 2-vinyl-4-methyl-4-nonyl-1,3-oxazolin-5-one, 2-isopropenyl-4-methyl-4-phenyl-1,3-oxazolin-5-one, 2-isopropenyl-4-methyl-4-benzyl-1,3-oxazolin-5-one, 2-vinyl-4,4-pentamethylene-1,3-oxazolin-5-one, and 2-vinyl-4,4-dimethyl-1,3-oxazolin-6-one (with 2-vinyl-4,4-dimethyl-1,3-oxazolin-5-one (VDMO) and 2-isopropenyl-4,4-dimethyl-1,3-oxazolin-5-one (IPDMO) as most preferred azlactone-containing vinylic monomers).

The reactions conditions for the above described coupling reactions are taught in textbooks and are well known to a person skilled in the art.

This aspect of the invention also is related to another class of azetidinium-containing vinylic monomers of the invention represented by formula (2)

An azetidinium-containing vinylic monomer of the invention can find particular use in preparing copolymers suitable for forming non-silicone hydrogel coatings on SiHy contact lenses and/or for forming an anchoring prime coating on SiHy contact lenses.

The invention, in another aspect, provides an azetidinium-containing copolymer comprising azetidinium-containing monomeric units derived from at least one vinylic monomer having an azetidinium group (preferably from an azetidinium-containing vinylic monomer of formula (1) or (2) as described above) and monomeric units derived from at least one vinylic monomer selected from the group consisting of a carboxyl-containing vinylic monomer, an amino-containing vinylic monomer, a hydrophobic vinylic monomer, and combination thereof.

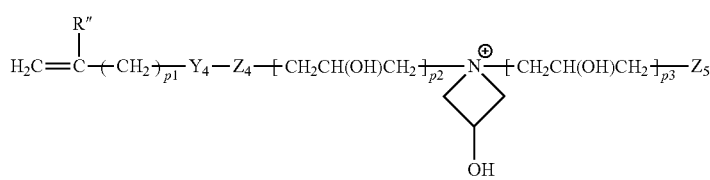

(2)

in which: p1, p2, and p3 independent of one another are zero or 1; R" is hydrogen or methyl; $Y_4$ is a linkage selected from the group consisting of a direct bond, —O—, —NR'—, —C(O)—NR'—, —NR'—C(O)—, —O—C(O)—NH—, —NH—C(O)—O—, —NR'—C(O)—NH—, —NH—C(O)—NR'—, —C(O)—O—, —O—C(O)—, R' is hydrogen, a $C_1$-$C_{20}$ unsubstituted or substituted, linear or branched alkyl group; $Z_4$, is a direct bond, a $C_1$-$C_{20}$ unsubstituted or substituted, linear or branched alkylene divalent radical optionally containing therein one or more linkages of —O—, —NR'—, and —C(O)—, a $C_1$-$C_7$ alkyleneoxy $C_1$-$C_7$ alkylene divalent radical, or a divalent radical of —(CH(R")CH$_2$O)$_{r1}$—CH(R")CH$_2$— in which R" is as defined above and r1 is an integer of 1 to 20; and $Z_5$ is a $C_1$-$C_{20}$ unsubstituted or substituted, linear or branched alkyl group, —(CH$_2$)$_{r2}$—O—(CH$_2$CH$_2$O)$_{r1}$—$Z_6$ in which r1 is as defined above, r2 is zero or an integer of 1 to 7, and $Z_6$ is a $C_1$-$C_5$ alkyl.

This class of azetidinium-containing vinylic monomers can be prepared by reacting epichlorohydrin directly with a vinylic monomer having a secondary amine group (—NH—) under reaction conditions known to a person skilled in the art. Examples of vinylic monomers includes without limitation: N-allyl $C_1$-$C_{12}$ alkanamine (e.g., N-ethyl-2-methylallylamine, N-ethylallylamine, N-allylmethylamine, N-allyl-1-pentanamine, N-allyl-2-methyl-1-pentanamine, N-Allyl-2,3-dimethyl-1-pentanamine, N-allyl-1-hexanamine, N-allyl-2-methyl-1-hexanamine, N-allyl-1-heptanamine, N-allyl-1-octanamine, N-allyl-1-ecanamine, N-allyl-1-dodecanamine); a secondary amine-containing vinylic monomer which is obtained either by reacting an epoxy compound having one sole epoxy group (e.g., 1,2-epoxy $C_3$-$C_{12}$ alkanes, or mono-epoxy terminated polyethyleneglycol) with allylamine, vinylamine, amino-$C_2$-$C_6$ alkyl (meth)acrylate, or amino-$C_2$-$C_6$ alkyl (meth)acrylamide or by reacting an $C_1$-$C_{12}$ alkanamine or amino-$C_2$-$C_{12}$ alkanol or with an epoxy-containing vinylic monomer (e.g., glycidyl (meth)acrylate, vinyl glycidyl ether, or allyl glycidyl ether) under coupling reaction conditions well known to a person skilled in the art.

Examples of preferred carboxyl-containing vinylic monomers include without limitation acrylic acid, a $C_1$-$C_4$-alkyl acrylic acid (e.g., methacrylic acid, ethylacrylic acid, propylacrylic acid, butylacrylic acid), N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carobxy-4-phenyl butadiene-1,3, itaconic acid, citraconic acid, mesaconic acid, glutaconic acid, aconitic acid, maleic acid, fumaric acid, and combination thereof.

Examples of preferred amino-containing vinylic monomers include amino-$C_2$-$C_4$ alkyl (meth)acrylate, allylamine, vinylamine, amino-$C_1$-$C_4$ alkyl (meth)acrylamide, N-allyl $C_1$-$C_{12}$ alkanamine (e.g., N-ethyl-2-methylallylamine, N-ethylallylamine, N-allylmethylamine, N-allyl-1-pentanamine, N-allyl-2-methyl-1-pentanamine, N-allyl-2,3-dimethyl-1-pentanamine, N-allyl-1-hexanamine, N-allyl-2-methyl-1-hexanamine, N-allyl-1-heptanamine, N-allyl-1-octanamine, N-allyl-1-ecanamine, N-allyl-1-dodecanamine), a coupling reaction product of an epoxy compound having one sole epoxy group (e.g., 1,2-epoxy $C_3$-$C_{12}$ alkanes, or mono-epoxy terminated polyethyleneglycol) with allylamine, vinylamine, amino-$C_2$-$C_6$ alkyl (meth)acrylate, or amino-$C_2$-$C_6$ alkyl (meth)acrylamide, a coupling reaction product of an $C_1$-$C_{12}$ alkanamine or $C_2$-$C_{12}$ aminoalkanol or with an epoxy-containing vinylic monomer (e.g., glycidyl (meth)acrylate, vinyl glycidyl ether, or allyl glycidyl ether), and combinations thereof.

Examples of preferred hydrophobic vinylic monomers include methyl (meth)acrylate, ethyl (meth)acrylate, propyl (meth)acrylate, isopropyl (meth)acrylate, butyl (meth)acrylate, sec-butyl (meth)acrylate, isobutyl (meth)acrylate, t-butyl (meth)acrylate, cyclohexylacrylate, 2-ethylhexylacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate, siloxane-containing vinylic monomer, a polysiloxane-containing vinylic monomer (having about 3 to about 40 silicone atoms), and combinations thereof.

Examples of preferred siloxane-containing vinylic monomers include N-[tris(trimethylsiloxy)silylpropyl]-(meth)acrylamide, N-[tris(dimethylpropyl-siloxy)silylpropyl] (meth)acrylamide, N-[tris(dimethylphenylsiloxy)-silylpropyl] (meth)acrylamide, N-[tris(dimethylethylsiloxy)silylpropyl] (meth)acrylamide, N-(2-hydroxy-3-(3-(bis(trimethylsilyloxy)methylsilyl)propyloxy) propyl)-2-methyl acrylamide, N-(2-hydroxy-3-(3-(bis(trimethylsilyloxy) methylsilyl)propyloxy)propyl) acrylamide, N,N-bis[2-hydroxy-3-(3-(bis(trimethylsilyloxy) methylsilyl)propyloxy) propyl]-2-methyl acrylamide, N,N-bis[2-hydroxy-3-(3-(bis(trimethylsilyloxy)methylsilyl)propyloxy)propyl] acrylamide, N-(2-hydroxy-3-(3-(tris(trimethylsilyloxy)silyl)-propyloxy)propyl)-2-methyl acrylamide, N-(2-hydroxy-3-(3-(tris(trimethylsilyloxy)silyl)propyloxy)-propyl) acrylamide, N,N-bis[2-hydroxy-3-(3-(tris(trimethylsilyloxy)silyl)propyloxy)propyl]-2-methyl acrylamide, N,N-bis[2-hydroxy-3-(3-(tris(trimethylsilyloxy)silyl)propyloxy)propyl]acrylamide, N-[2-hydroxy-3-(3-(t-butyldimethylsilyl)oxy)propyl]-2-methyl acrylamide, N-[2-hydroxy-3-(3-(t-butyldimethylsilyl) propyloxy)propyl]acrylamide, N,N-bis[2-hydroxy-3-(3-(t-butyldimethylsilyl)-propyloxy)propyl]-2-methyl acrylamide, N,N-bis[2-hydroxy-3-(3-(t-butyldimethylsilyl)propyloxy)-propyl] acrylamide, 3-methacryloxy propylpentamethyldisiloxane, tris(trimethylsilyloxy)silylpropyl methacrylate (TRIS), (3-methacryloxy-2-hydroxypropyloxy)propylbis(trimethylsiloxy)-methylsilane), (3-methacryloxy-2-hydroxypropyloxy)propyltris(trimethylsiloxy)silane, 3-methacryloxy-2-(2-hydroxyethoxy)-propyloxy)propylbis(trimethylsiloxy) methylsilane, N-2-methacryloxyethyl-O-(methyl-bis-trimethylsiloxy-3-propyl)silyl carbamate, 3-(trimethylsilyl)-propylvinyl carbonate, 3-(vinyloxycarbonylthio)propyl-tris (trimethyl-siloxy)silane, 3-[tris(trimethylsiloxy)silyl] propylvinyl carbamate, 3-[tris(trimethylsiloxy)silyl] propyl allyl carbamate, 3-[tris(trimethylsiloxy)silyl]propyl vinyl carbonate, t-butyldimethyl-siloxyethyl vinyl carbonate, trimethylsilylethyl vinyl carbonate, trimethylsilylmethyl vinyl carbonate, and combinations thereof.

A "polysiloxane-containing vinylic monomer" refers to a vinylic monomer comprising one sole ethylenically-unsaturated group and at least one poly(di-$C_1$-$C_6$ alkyl-substituted siloxane) segment. Examples of preferred polysiloxane-containing vinylic monomer having about 3 to about 40 silicone atoms include mono-(meth)acrylate-terminated polydimethylsiloxanes of various molecular weight (e.g., mono-3-methacryloxypropyl terminated, mono-$C_1$-$C_4$ alkyl terminated polydimethylsiloxane, or mono-(3-methacryloxy-2-hydroxypropyloxy)propyl terminated, mono-$C_1$-$C_4$ alkyl terminated polydimethylsiloxane), mono-vinyl-terminated polydimethylsiloxanes, mono-(meth)acrylamide-terminated polydimethylsiloxanes, mono-vinylcarbamate-terminated polydimethylsiloxanes, mono-vinylcarbonate-terminated polydimethylsiloxanes, and combinations thereof. Alternatively, monoethylenically functionalized polysiloxanes can be obtained by ethylenically functionalizing of a monofunctionalized polysiloxanes (i.e., with one sole terminal functional group, such as, e.g., —$NH_2$, —OH, —COOH, epoxy group, halide, etc.) as described above. Suitable monofunctionalized polysiloxanes are commercially available, e.g., from Aldrich, ABCR GmbH & Co., Fluorochem, or Gelest, Inc, Morrisville, Pa.

It is reported that the hydrogen dissociation constants (pKa) are about 4.0 for polyacrylic acid, about 5.3 for polymethacrylic acid, about 6.3 for polyethylacrylic acid, about 6.7 for polypropylacrylic acid, and about 7.4 for polybutylacrylic acid (see, H. Dong, *J. Phys. Chem. A* 112 (49): 12687-12694 (2008); F. Mitsuko, R. Grubbs, and J. D. Baldeschwieler, *J. Colloid Interface Sci.* 185: 210-216 (1997); S. J. Grainger and E. H. El-Sayed, in Biologically-Responsive Hybrid Biomaterials: A Reference for Material Scientists and Bioengineers, E. Jabbari et A. Khademhosseini, Eds., Boston, Mass.: Artech Publishing (2010), Chapter 7, pp 171-190). Because of the differences in pKa, the ionization degrees of the carboxyl groups of those polymers at neutral pH can be significantly different and can have different levels of uptake of positively-charged antimicrobial agents (e.g., PHMB, aldox, POLYQUAD, etc.) present in lens care solutions. It is believed that where the azetidinium-containing polymer for a coating on a SiHy contact lens is composed primarily of methacrylic acid or ethylacrylic acid, the uptake of those positively-charged antimicrobial agents present in lens care solutions can be minimized.

In a preferred embodiment, an azetidinium-containing copolymer of the invention preferably comprises: azetidinium-containing monomeric units derived from at least one azetidinium-containing vinylic monomer of formula (1) or (2) (as described above); and carboxyl-containing monomeric units derived from a carboxyl-containing vinylic monomer (preferably selected from the group consisting of acrylic acid, methacrylic acid, ethylacrylic acid, propylacrylic acid, maleic acid, and combinations thereof, more preferably selected from the group consisting of methacrylic acid, ethylacrylic acid, and combination thereof, even more preferably derived from methacrylic acid); and optionally amino-containing monomeric units derived from at least one amino-containing vinylic monomer [preferably selected from the group consisting of amino-$C_2$-$C_4$ alkyl (meth)acrylate, allylamine, vinylamine, amino-$C_1$-$C_4$ alkyl (meth)acrylamide, N-allyl $C_1$-$C_{12}$ alkanamine (e.g., N-ethyl-2-methylallylamine, N-ethylallylamine, N-allylmethylamine, N-allyl-1-pentanamine, N-allyl-2-methyl-1-pentanamine, N-allyl-2,3-dimethyl-1-pentanamine, N-allyl-1-hexanamine, N-allyl-2-methyl-1-hexanamine, N-allyl-1-heptanamine, N-allyl-1-octanamine, N-allyl-1-ecanamine, N-allyl-1-dodecanamine), a coupling reaction product of an epoxy compound having one sole epoxy group (e.g., 1,2-epoxy $C_3$-$C_{12}$ alkanes, or mono-epoxy terminated polyethyleneglycol) with allylamine, vinylamine, amino-$C_2$-$C_6$ alkyl (meth)acrylate, or amino-$C_2$-$C_6$ alkyl (meth)acrylamide, a coupling reaction product of an $C_1$-$C_{12}$ alkanamine or $C_2$-$C_{12}$ aminoalkanol or with an epoxy-containing vinylic monomer (e.g., glycidyl (meth)acrylate, vinyl glycidyl ether, or allyl glycidyl ether), and combinations thereof].

In another preferred embodiment, an azetidinium-containing copolymer of the invention preferably comprises: azetidinium-containing monomeric units derived from at least one azetidinium-containing vinylic monomer of formula (1) or (2) (as described above); carboxyl-containing monomeric units derived from a carboxyl-containing vinylic monomer preferably selected from the group consisting of acrylic acid, methacrylic acid, ethylacrylic acid, propylacrylic acid, maleic acid, and combinations thereof (more preferably selected from the group consisting of methacrylic acid, ethylacrylic acid, and combination thereof, even more preferably derived from methacrylic acid); and hydrophobic monomeric units derived from at least one hydrophobic vinylic monomer (preferably selected from the group consisting of methyl (meth)acrylate, ethyl (meth)acrylate, propyl (meth)acrylate, isopropyl (meth)acrylate, butyl (meth)acrylate, sec-butyl (meth)acrylate, isobutyl (meth)acrylate, t-butyl (meth)acrylate, cyclohexylacrylate, 2-ethylhexylacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate, siloxane-containing vinylic monomer, a polysiloxane-containing vinylic monomer having about 3 to about 40 silicone atoms, and combinations thereof, more preferably selected from the group consisting of at least one siloxane-containing vinylic monomer, at least one polysiloxane-containing vinylic monomer and combinations thereof); and optionally amino-containing monomeric units derived from at least one amino-containing vinylic monomer [preferably selected from the group consisting of amino-$C_2$-$C_4$ alkyl (meth)acrylate, allylamine, vinylamine, amino-$C_1$-$C_4$ alkyl (meth)acrylamide, N-allyl $C_1$-$C_{12}$ alkanamine (e.g., N-ethyl-2-methylallylamine, N-ethylallylamine, N-allylmethylamine, N-allyl-1-pentanamine, N-allyl-2-methyl-1-pentanamine, N-allyl-2,3-dimethyl-1-pentanamine, N-allyl-1-hexanamine, N-allyl-2-methyl-1-hexanamine, N-allyl-1-heptanamine, N-allyl-1-octanamine, N-allyl-1-ecanamine, N-allyl-1-dodecanamine), a coupling reaction product of an epoxy compound having one sole epoxy group (e.g., 1,2-epoxy $C_3$-$C_{12}$ alkanes, or mono-epoxy terminated polyethyleneglycol) with allylamine, vinylamine, amino-$C_2$-$C_6$ alkyl (meth)acrylate, or amino-$C_2$-$C_6$ alkyl (meth)acrylamide, a coupling reaction product of an $C_1$-$C_{12}$ alkanamine or $C_2$-$C_{12}$ aminoalkanol or with an epoxy-containing vinylic monomer (e.g., glycidyl (meth)acrylate, vinyl glycidyl ether, or allyl glycidyl ether), and combinations thereof].

In another preferred embodiment, an azetidinium-containing copolymer of the invention preferably comprises: azetidinium-containing monomeric units derived from at least one azetidinium-containing vinylic monomer of formula (1) or (2) (as described above); hydrophobic monomeric units derived from at least one hydrophobic vinylic monomer (preferably selected from the group consisting of methyl (meth)acrylate, ethyl (meth)acrylate, propyl (meth)acrylate, isopropyl (meth)acrylate, butyl (meth)acrylate, sec-butyl (meth)acrylate, isobutyl (meth)acrylate, t-butyl (meth)acrylate, cyclohexylacrylate, 2-ethylhexylacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate, siloxane-containing vinylic monomer, a polysiloxane-containing vinylic monomer having about 3 to about 40 silicone atoms, and combinations thereof, more preferably selected from the group consisting of at least one siloxane-containing vinylic monomer, at least one polysiloxane-containing vinylic monomer, and combinations thereof); and optionally amino-containing monomeric units derived from at least one amino-containing vinylic monomer [preferably selected from the group consisting of amino-$C_2$-$C_4$ alkyl (meth)acrylate, allylamine, vinylamine, amino-$C_1$-$C_4$ alkyl (meth)acrylamide, N-allyl $C_1$-$C_{12}$ alkanamine (e.g., N-ethyl-2-methylallylamine, N-ethylallylamine, N-allylmethylamine, N-allyl-1-pentanamine, N-allyl-2-methyl-1-pentanamine, N-allyl-2,3-dimethyl-1-pentanamine, N-allyl-1-hexanamine, N-allyl-2-methyl-1-hexanamine, N-allyl-1-heptanamine, N-allyl-1-octanamine, N-allyl-1-ecanamine, N-allyl-1-dodecanamine), a coupling reaction product of an epoxy compound having one sole epoxy group (e.g., 1,2-epoxy $C_3$-$C_{12}$ alkanes, or mono-epoxy terminated polyethyleneglycol) with allylamine, vinylamine, amino-$C_2$-$C_6$ alkyl (meth)acrylate, or amino-$C_2$-$C_6$ alkyl (meth)acrylamide, a coupling reaction product of an $C_1$-$C_{12}$ alkanamine or $C_2$-$C_{12}$ aminoalkanol or with an epoxy-containing vinylic monomer (e.g., glycidyl (meth)acrylate, vinyl glycidyl ether, or allyl glycidyl ether), and combinations thereof].

In another preferred embodiment, an azetidinium-containing copolymer of the invention preferably comprises: (1) azetidinium-containing monomeric units derived from at least one azetidinium-containing vinylic monomer of formula (1) or (2) (as described above); (2) reactive monomeric units which are carboxyl-containing monomeric units and/or amino-containing monomeric units, wherein the carboxyl-containing monomeric units are derived from at least one carboxyl-containing vinylic monomer (any one of the those described above) and wherein the amino-containing vinylic monomeric units are derived from at least one amino-containing vinylic monomer (any one of those described above); and (3) at least about 50%, preferably at least about 60%, more preferably at least about 70%, even more preferably at least about 75% by moles of non-reactive hydrophilic monomeric units derived from at least one hydrophilic vinylic monomer selected from the group consisting of (meth)acrylamide, N,N-dimethyl (meth)acrylamide, N-vinylpyrrolidone, N,N,-dimethylaminoethyl (meth)acrylate, N,N-dimethylaminopropyl (meth)acrylamide, glycerol methacrylate, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, hydroxypropyl (meth)acrylate, $C_1$-$C_4$-alkoxy polyethylene glycol (meth)acrylate having a weight average molecular weight of up to 1500 Daltons, N-vinyl formamide, N-vinyl acetamide, N-vinyl isopropylamide, N-vinyl-N-methyl acetamide, allyl alcohol, vinyl alcohol (hydrolyzed form of vinyl acetate in the copolymer), a phosphorylcholine-containing vinylic monomer (including (meth)acryloyloxyethyl phosphorylcholine and those described in U.S. Pat. No. 5,461,433, herein incorporated by reference in its entirety), a sugar-containing vinylic monomer (e.g., erythritol (meth)acrylate, arabitol (meth)acrylate, mannitol (meth)acrylate, ducitol (meth)acrylate, fucitol (meth)acrylate, iditol (meth)acrylate, innositol (meth)acrylate, xylitol (meth)acrylate, sorbitol (meth)acrylate, glucose (meth)acrylate, fructose (meth)acrylate, galactose (meth) acrylate, and combinations thereof (preferably selected from the group consisting of (meth)acrylamide, N,N-dimethyl (meth)acrylamide, N-vinylpyrrolidone, N,N,-dimethylaminoethyl (meth)acrylate, glycerol methacrylate, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth) acrylate, $C_1$-$C_4$-alkoxy polyethylene glycol (meth)acrylate having a weight average molecular weight of up to 1500 Daltons, N-vinyl formamide, N-vinyl acetamide, N-vinyl-N-methyl acetamide, allyl alcohol, a phosphorylcholine-containing vinylic monomer (including (meth)acryloyloxyethyl phosphorylcholine and those described in U.S. Pat. No. 5,461,433, herein incorporated by reference in its entirety), erythritol (meth)acrylate, arabitol (meth)acrylate, mannitol (meth)acrylate, ducitol (meth)acrylate, fucitol (meth)acrylate, iditol (meth)acrylate, innositol (meth)acrylate, xylitol (meth)acrylate, sorbitol (meth)acrylate, glucose (meth)acrylate, fructose (meth)acrylate, galactose (meth)acrylate, and combinations thereof). More preferably, the copolymer comprises up to about 50%, preferably from about 2.5% to about 40%, more preferably from about 5% to about 30%, even more preferably from about 7.5% to about 25% by moles of azetidinium-containing monomeric units and reactive monomeric units.

The weight average molecular weight $M_w$ of an azetidinium-containing copolymer of the invention is at least about 10,000 Daltons, preferably at least about 50,000 Daltons, more preferably at least about 100,000 Daltons, even more preferably from about 200,000 to about 1,000,000 Daltons.

A person skilled in the art knows well how to prepare an azetidinium-containing copolymer of the invention according to any known polymerization technique.

An azetidinium-containing copolymer of the invention can find particular use in forming crosslinked hydrophilic coatings on SiHy contact lenses.

The invention, in a further aspect, provides a method for producing coated silicone hydrogel contact lenses each having a crosslinked hydrophilic coating thereon, the method of invention comprising the steps of: (a) obtaining a silicone hydrogel contact lens; (b) applying a prime coating of an anchoring polymer onto the silicone hydrogel contact lens, wherein the anchoring polymer is a homopolymer or copolymer of a carboxyl-containing vinylic monomer and/or an azetidinium-containing copolymer which comprises first azetidinium-containing monomeric units derived from at least one azetidinium-containing vinylic monomer (preferably of formula (1) or (2) as described above) and monomeric units selected from the group consisting of carboxyl-containing monomeric units derived from at least one carboxyl-containing vinylic monomer (any one of those described above), amino-containing monomeric units derived from at least one amino-containing vinylic monomer (any one of those described above), hydrophobic monomeric units derived from at least one hydrophobic vinylic monomer (any one of those described above), and combinations thereof; and (c) heating the silicone hydrogel contact lens in an aqueous solution in the presence of a water-soluble, thermally-crosslinkable hydrophilic polymeric material comprising reactive functional groups selected from the group consisting of azetidinium groups, carboxyl groups, amino groups, thiol groups and combinations thereof, to and at a temperature from about 40° C. to about 140° C. for a period of time sufficient to induce intermolecular and intramolecular crosslinking reaction between one azetidinium group and one amino or carboxyl group, thereby forming a durable non-silicone hydrogel coating on the silicone hydrogel contact lens, provided that at least one of the anchoring polymer and the thermally crosslinkable hydrophilic polymeric material comprises azetidinium groups.

A person skilled in the art knows very well how to make contact lenses. For example, contact lenses can be produced in a conventional "spin-casting mold," as described for example in U.S. Pat. No. 3,408,429, or by the full cast-molding process in a static form, as described in U.S. Pat. Nos. 4,347,198; 5,508,317; 5,583,463; 5,789,464; and 5,849,810, or by lathe cutting of silicone hydrogel buttons as used in making customized contact lenses. In cast-molding, a lens formulation typically is dispensed into molds and cured (i.e., polymerized and/or crosslinked) in molds for making contact lenses. For production of silicone hydrogel (SiHy) contact lenses, a SiHy lens-forming composition (or SiHy lens formulation) for cast-molding or spin-cast molding or for making SiHy rods used in lathe-cutting of contact lenses generally comprises at least one components selected from the group consisting of a silicone-containing vinylic monomer, a silicone-containing vinylic macromer, a silicone-containing prepolymer, a hydrophilic vinylic monomer, a hydrophobic vinylic monomer, a crosslinking agent (a compound having a molecular weight of about 700 Daltons or less and containing at least two ethylenically unsaturated groups), a free-radical initiator (photoinitiator or thermal initiator), a hydrophilic vinylic macromer/prepolymer, and combination thereof, as well known to a person skilled in the art. A SiHy contact lens formulation can also comprise other necessary components known to a person skilled in the art, such as, for example, a UV-absorbing agent, a visibility tinting agent (e.g., dyes, pigments, or mixtures thereof), antimicrobial agents (e.g., preferably silver nanoparticles), a bioactive agent, leachable lubricants, leachable tear-stabilizing agents, and mixtures thereof, as known to a person skilled in the art. Resultant SiHy contact lenses then can be subjected to extraction with an extraction solvent to remove unpolymerized components from the resultant lenses and to hydration process, as known by a person skilled in the art. In addition, a preformed SiHy contact lens can be a colored contact lens (i.e., a SiHy contact lens having at least one colored patterns printed thereon as well known to a person skilled in the art).

Numerous SiHy lens formulations including various combinations of components described above have been described in numerous patents and patent applications published by the filing date of this application. All of them can be used in obtaining a SiHy lens to be coated. A SiHy lens formulation for making commercial SiHy lenses, such as, lotrafilcon A, lotrafilcon B, delefilcon A, balafilcon A, galyfilcon A, senofilcon A, narafilcon A, narafilcon B, comfilcon A, enfilcon A, asmofilcon A, or the like, can also be used in making SiHy contact lenses to be coated in this invention.

In accordance with the invention, a prime coating is formed by contacting a SiHy contact lens (to be coated) with a solution of an anchoring polymer. Contacting of the contact lens with a solution of an anchoring polymer can occur by dipping it into the coating solution or by spraying it with the coating solution. One contacting process involves solely dipping the contact lens in a bath of a solution of the anchoring polymer for a period of time or alternatively dipping the contact lens sequentially in a series of bath of solutions of the anchoring polymer for a fixed shorter time period for each bath. Another contacting process involves solely spray a solution of the anchoring polymer. However, a number of alternatives involve various combinations of spraying- and dipping-steps may be designed by a person having ordinary skill in the art.

The contacting time of a contact lens with a solution of the anchoring polymer may last up to about 10 minutes, preferably from about 5 to about 360 seconds, more preferably from about 5 to about 250 seconds, even more preferably from about 5 to 200 seconds.

In accordance with the invention, the anchoring polymer is a linear or branched or crosslinked polymer, so long as it is soluble in water, an organic solvent, a mixture of two or more organic solvents, a mixture of water with one or more organic solvent.

All the embodiments and preferred embodiments of carboxyl-containing vinylic monomers, azetidinium-containing vinylic monomers, amino-containing vinylic monomers, hydrophobic vinylic monomers, non-reactive hydrophilic vinylic monomers, and azetidinium-containing copolymers have been described above and can be used in this aspect of the invention.

In a preferred embodiment, an anchoring polymer of the invention preferably comprises carboxyl-containing monomeric units derived from a carboxyl-containing vinylic monomer preferably selected from the group consisting of acrylic acid, methacrylic acid, ethylacrylic acid, propylacrylic acid, maleic acid, and combinations thereof, more preferably selected from the group consisting of methacrylic acid, ethylacrylic acid, and combination thereof, even more preferably derived from methacrylic acid.

In another preferred embodiment, the anchoring polymer is: polyacrylic acid (PAA); polymethacrylic acid (PMAA); polyethylacrylic acid, polypropylacrylic acid; a copolymer of at least two vinylic monomers selected from the group consisting of acrylic acid, methacrylic acid, ethylacrylic acid, and propylacrylic acid; polymaleic acid (i.e., partially or fully hydrolyzed polymaleic anhydride); a copolymer of maleic acid and one or more vinylic monomers (e.g., ethylene, methyl vinyl ether, vinyl acetate, and/or isobutylene); a copolymer composed of from about 0.05% to about 20% (preferably from about 0.1% to about 15%, more preferably from about 0.5% to about 10%) by moles of an azetidinium-containing vinylic monomer (preferably an azetidinium-containing vinylic monomer of formula (1) as described above) and of from about 80% to about 99.95% by moles of one or more carboxyl-containing vinylic monomers selected from the group consisting of acrylic acid, methacrylic acid, ethylacrylic acid, propylacrylic acid, and combination thereof; a reaction product of an azetidinium compound of

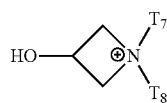

in which $T_7$ and $T_8$ as defined above with polymaleic anhydride or with a copolymer of maleic anhydride and one or more vinylic monomers (e.g., ethylene, methyl vinyl ether, vinyl acetate, and/or isobutylene), wherein the molar equivalent ratio of the azetidinium compound to maleic anhydride is about 0.25 or less (preferably about 0.2 or less, more preferably about 0.15 or less, even more preferably about 0.1 or less); and combinations thereof.

In another preferred embodiment, an anchoring polymer of the invention preferably comprises: carboxyl-containing monomeric units derived from a carboxyl-containing vinylic monomer preferably selected from the group consisting of acrylic acid, methacrylic acid, ethylacrylic acid, propylacrylic acid, maleic acid, and combinations thereof (more preferably selected from the group consisting of methacrylic acid, ethylacrylic acid, and combination thereof, even more preferably derived from methacrylic acid); and azetidinium-containing monomeric units derived from at least one azetidinium-containing vinylic monomer of formula (1) or (2) (as described above).

In another preferred embodiment, an anchoring polymer of the invention preferably comprises: carboxyl-containing monomeric units derived from a carboxyl-containing vinylic monomer preferably selected from the group consisting of acrylic acid, methacrylic acid, ethylacrylic acid, propylacrylic acid, maleic acid, and combinations thereof (more preferably selected from the group consisting of methacrylic acid, ethylacrylic acid, and combination thereof, even more preferably derived from methacrylic acid); azetidinium-containing monomeric units derived from at least one azetidinium-containing vinylic monomer of formula (1) or (2) (as described above); and hydrophobic monomeric units derived from at least one hydrophobic vinylic monomer (preferably from at least one siloxane-containing vinylic monomer and/or at least one polysiloxane-containing vinylic monomer).

In another preferred embodiment, an anchoring polymer of the invention preferably comprises: azetidinium-containing monomeric units derived from at least one azetidinium-containing vinylic monomer of formula (1) or (2) (as described above); and hydrophobic monomeric units derived from at least one hydrophobic vinylic monomer (preferably from at least one siloxane-containing vinylic monomer and/or at least one polysiloxane-containing vinylic monomer).

In another preferred embodiment, an anchoring polymer of the invention preferably comprises: carboxyl-containing monomeric units derived from a carboxyl-containing vinylic monomer preferably selected from the group consisting of acrylic acid, methacrylic acid, ethylacrylic acid, propylacrylic acid, maleic acid, and combinations thereof (more preferably selected from the group consisting of methacrylic acid, ethylacrylic acid, and combination thereof, even more preferably derived from methacrylic acid); and and hydrophobic monomeric units derived from at least one hydrophobic vinylic monomer (preferably from at least one siloxane-containing vinylic monomer and/or at least one polysiloxane-containing vinylic monomer).

The weight average molecular weight $M_w$ of an anchoring polymer for forming an anchoring prime coating is at least about 10,000 Daltons, preferably at least about 50,000 Daltons, more preferably at least about 100,000 Daltons, even more preferably from about 200,000 to about 1,000,000 Daltons.

A solution of an anchoring polymer for forming a prime coating on contact lenses can be prepared by dissolving one or more anchoring polymers in water, a mixture of water and an organic solvent miscible with water, an organic solvent, or a mixture of one or more organic solvent. Preferably, the anchoring polymer is dissolved in a mixture of water and one or more organic solvents, an organic solvent, or a mixture of one or more organic solvent. It is believed that a solvent system containing at least one organic solvent can swell a silicone hydrogel contact lens so that a portion of the anchoring polymer may penetrate into the silicone hydrogel contact lens and increase the durability of the prime coating.

Any organic solvents can be used in preparation of a solution of an anchoring polymer. Examples of organic solvents include without limitation tetrahydrofuran, tripropylene glycol methyl ether, dipropylene glycol methyl ether, ethylene glycol n-butyl ether, ketones (e.g., acetone, methyl ethyl ketone, etc.), diethylene glycol n-butyl ether, diethylene glycol methyl ether, ethylene glycol phenyl ether, propylene glycol methyl ether, propylene glycol methyl ether acetate, dipropylene glycol methyl ether acetate, propylene glycol n-propyl ether, dipropylene glycol n-propyl ether, tripropylene glycol n-butyl ether, propylene glycol n-butyl ether, dipropylene glycol n-butyl ether, tripropylene glycol n-butyl ether, propylene glycol phenyl ether dipropylene glycol dimetyl ether, polyethylene glycols, polypropylene glycols, ethyl acetate, butyl acetate, amyl acetate, methyl lactate, ethyl lactate, i-propyl lactate, methylene chloride, methanol, ethanol, 1- or 2-propanol, 1- or 2-butanol, tert-butanol, tert-amyl alcohol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, 1-ethoxy-2-propanol, 1-methyl-2-pyrrolidone, N,N-dimethylpropionamide, dimethyl formamide, dimethyl acetamide, dimethyl propionamide, N-methyl pyrrolidinone, and mixtures thereof.

In accordance with this aspect of the invention, wherein the water-soluble, thermally-crosslinkable hydrophilic polymeric material can be any water-soluble polymer so long as it contains reactive groups selected from the group consisting of azetidinium groups, carboxyl groups, amino groups, thiol groups, and combinations thereof. Preferably, a water-soluble, thermally crosslinkable hydrophilic polymeric material is: (i) an azetidinium-containing copolymer of the invention (as those described above and can be used here) comprising comprises at least about 50%, preferably at least about 60%, more preferably at least about 70%, even more preferably at least about 75% by moles of non-reactive hydrophilic monomeric units derived from at least one hydrophilic vinylic monomer (any one of those described above); (ii) a reaction product of an azetidinium-containing copolymer (as those described above and can be used here) being free of any silicone with at least one hydrophilicity-enhancing agent having at least one reactive functional group selected from the group consisting of amino group, carboxyl group, thiol group, and combinations thereof; (iii) a reaction product of polyaminoamide-epichlorohydrin with at least one hydrophilicity-enhancing agent having at least one reactive functional group selected from the group consisting of amino group, carboxyl group, thiol group, and combinations thereof; and (iv) a water-soluble hydrophilic polymer having at least one reactive functional group selected from the group consisting of amino group, carboxyl group, thiol group, and combinations thereof.

The term "hydrophilicity-enhancing agent" refers to a hydrophilic organic compound or polymer that can reacted with an azetidinium-containing copolymer of the invention to form a product with the hydrophilicity-enhancing agent covalently incorporated therein as hydrophilic moieties and/or hydrophilic chains. Any suitable hydrophilicity-enhancing agents can be used in the invention so long as they contain at least one amino group, at least one carboxyl group, and/or at least one thiol group.

A preferred class of hydrophilicity-enhancing agents include without limitation: amino-, carboxyl- or thiol-containing monosaccharides (e.g., 3-amino-1,2-propanediol, 1-thiolglycerol, 5-keto-D-gluconic acid, galactosamine, glucosamine, galacturonic acid, gluconic acid, glucosaminic acid, mannosamine, saccharic acid 1,4-lactone, saccharide acid, Ketodeoxynonulosonic acid, N-methyl-D-glucamine, 1-amino-1-deoxy-β-D-galactose, 1-amino-1-deoxysorbitol, 1-methylamino-1-deoxysorbitol, N-aminoethyl gluconamide); amino-, carboxyl- or thiol-containing disaccharides (e.g., chondroitin disaccharide sodium salt, di(β-D-xylopyranosyl)amine, digalacturonic acid, heparin disaccharide, hyaluronic acid disaccharide, Lactobionic acid); and amino-, carboxyl- or thiol-containing oligosaccharides (e.g., carboxymethyl-β-cyclodextrin sodium salt, trigalacturonic acid); and combinations thereof.

Another preferred class of hydrophilicity-enhancing agents is hydrophilic polymers having one or more amino, carboxyl and/or thiol groups. More preferably, the content of monomeric units having an amino (—NHR' with R' as defined above), carboxyl (—COOH) and/or thiol (—SH) group in a hydrophilic polymer as a hydrophilicity-enhancing agent is less than about 40%, preferably less than about 30%, more preferably less than about 20%, even more preferably less than about 10%, by weight based on the total weight of the hydrophilic polymer.

One preferred class of hydrophilic polymers as hydrophilicity-enhancing agents are amino- or carboxyl-containing polysaccharides, for example, such as, carboxymethylcellulose (having a carboxyl content of about 40% or less, which is estimated based on the composition of repeating units, —[$C_6H_{10-m}O_5(CH_2CO_2H)_m$]— in which m is 1 to 3), carboxyethylcellulose (having a carboxyl content of about 36% or less, which is estimated based on the composition of repeating units, —[$C_6H_{10-m}O_5(C_2H_4CO_2H)_m$]— in which m is 1 to 3) carboxypropylcellulose (having a carboxyl content of about 32% or less, which is estimated based on the composition of repeating units, —[$C_6H_{10-m}O_5(C_3H_6CO_2H)_m$]—, in which m is 1 to 3), hyaluronic acid (having a carboxyl content of about 11%, which is estimated based on the composition of repeating units, —($C_{13}H_{20}O_9NCO_2H$)—), chondroitin sulfate (having a carboxyl content of about 9.8%, which is estimated based on the composition of repeating units, —($C_{12}H_{18}O_{13}NS CO_2H$)—), or combinations thereof.

Another preferred class of hydrophilic polymers as hydrophilicity-enhancing agents include without limitation: poly (ethylene glycol) (PEG) with mono-amino, carboxyl or thiol group (e.g., PEG-NH$_2$, PEG-SH, PEG-COOH); H$_2$N-PEG-NH$_2$; HOOC-PEG-COOH; HS-PEG-SH; H$_2$N-PEG-COOH; HOOC-PEG-SH; H$_2$N-PEG-SH; multi-arm PEG with one or more amino, carboxyl or thiol groups; PEG dendrimers with one or more amino, carboxyl or thiol groups; a diamino- or dicarboxyl-terminated homo- or copolymer of a non-reactive hydrophilic vinylic monomer; a monoamino- or monocarboxyl-terminated homo- or copolymer of a non-reactive hydrophilic vinylic monomer; a copolymer which is a polymerization product of a composition comprising (1) about 60% by weight or less, preferably from about 0.1% to about 30%, more preferably from about 0.5% to about 20%, even more preferably from about 1% to about 15%, by weight of one or more reactive vinylic monomers and (2) at least one non-reactive hydrophilic vinylic monomer and/or at least one phosphorylcholine-containing vinylic monomer; and combinations thereof. Reactive vinylic monomer(s) and non-reactive hydrophilic vinylic monomer(s) are those described previously.

More preferably, a hydrophilic polymer as a hydrophilicity-enhancing agent is PEG-NH$_2$; PEG-SH; PEG-COOH; H$_2$N-PEG-NH$_2$; HOOC-PEG-COOH; HS-PEG-SH; H$_2$N-PEG-COOH; HOOC-PEG-SH; H$_2$N-PEG-SH; multi-arm PEG with one or more amino, carboxyl or thiol groups; PEG dendrimers with one or more amino, carboxyl or thiol groups; a monoamino-, monocarboxyl-, diamino- or dicarboxyl-terminated homo- or copolymer of a non-reactive hydrophilic vinylic monomer selected from the group consisting of acrylamide (AAm), N,N-dimethylacrylamide (DMA), N-vinylpyrrolidone (NVP), N-vinyl-N-methyl acetamide, glycerol (meth)acrylate, hydroxyethyl (meth)acrylate, N-hydroxyethyl (meth)acrylamide, $C_1$-$C_4$-alkoxy polyethylene glycol (meth)acrylate having a weight average molecular weight of up to 400 Daltons, vinyl alcohol, N-methyl-3-methylene-2-pyrrolidone, 1-methyl-5-methylene-2-pyrrolidone, 5-methyl-3-methylene-2-pyrrolidone, N,N-dimethylaminoethyl (meth)acrylate, N,N-dimethylaminopropyl (metha)crylamide, (meth)acryloyloxyethyl phosphorylcholine, and combinations thereof; a copolymer which is a polymerization product of a composition comprising (1) from about 0.1% to about 30%, preferably from about 0.5% to about 20%, more preferably from about 1% to about 15%, by weight of (meth)acrylic acid, $C_2$-$C_{12}$ alkylacrylic acid, vinylamine, allylamine, and/or amino-$C_2$-$C_4$ alkyl (meth)acrylate, and (2) (meth)acryloyloxyethyl phosphorylcholine and/or at least one non-reactive hydrophilic vinylic monomer selected from the group consisting of acrylamide, N,N-dimethylacrylamide, N-vinylpyrrolidone, N-vinyl-N-methyl acetamide, glycerol (meth)acrylate, hydroxyethyl (meth)acrylate, N-hydroxyethyl (meth)acrylamide, $C_1$-$C_4$-alkoxy polyethylene glycol (meth)acrylate having a weight average molecular weight of up to 400 Daltons, vinyl alcohol, and combination thereof.

Most preferably, the hydrophilicity-enhancing agent as a hydrophilicity-enhancing agent is PEG-$NH_2$; PEG-SH; PEG-COOH; monoamino-, monocarboxyl-, diamino- or dicarboxyl-terminated polyvinylpyrrolidone; monoamino-, monocarboxyl-, diamino- or dicarboxyl-terminated polyacrylamide; monoamino-, monocarboxyl-, diamino- or dicarboxyl-terminated poly(DMA); monoamino- or monocarboxyl-, diamino- or dicarboxyl-terminated poly(DMA-co-NVP); monoamino-, monocarboxyl-, diamino- or dicarboxyl-terminated poly(NVP-co-N,N-dimethylaminoethyl (meth)acrylate)); monoamino-, monocarboxyl-, diamino- or dicarboxyl-terminated poly(vinylalcohol); monoamino-, monocarboxyl-, diamino- or dicarboxyl-terminated poly[(meth)acryloyloxyethyl phosphrylcholine] homopolymer or copolymer; monoamino-, monocarboxyl-, diamino- or dicarboxyl-terminated poly(NVP-co-vinyl alcohol); monoamino-, monocarboxyl-, diamino- or dicarboxyl-terminated poly(DMA-co-vinyl alcohol); poly[(meth)acrylic acid-co-acrylamide] with from about 0.1% to about 30%, preferably from about 0.5% to about 20%, more preferably from about 1% to about 15%, by weight of (meth)acrylic acid; poly[(meth)acrylic acid-co-NVP) with from about 0.1% to about 30%, preferably from about 0.5% to about 20%, more preferably from about 1% to about 15%, by weight of (meth)acrylic acid; a copolymer which is a polymerization product of a composition comprising (1) (meth)acryloyloxyethyl phosphorylcholine and (2) from about 0.1% to about 30%, preferably from about 0.5% to about 20%, more preferably from about 1% to about 15%, by weight of a carboxylic acid containing vinylic monomer and/or an amino-containing vinylic monomer, and combination thereof.

PEGs with functional groups and multi-arm PEGs with functional groups can be obtained from various commercial suppliers, e.g., Polyscience, and Shearwater Polymers, inc., etc.

Monoamino-, monocarboxyl-, diamino- or dicarboxyl-terminated homo- or copolymers of one or more non-reactive hydrophilic vinylic monomers or of a phosphorylcholine-containing vinylic monomer can be prepared according to procedures described in U.S. Pat. No. 6,218,508, herein incorporated by reference in its entirety. For example, to prepare a diamino- or dicarboxyl-terminated homo- or co-polymer of a non-reactive hydrophilic vinylic monomer, the non-reactive vinylic monomer, a chain transfer agent with an amino or carboxyl group (e.g., 2-aminoethanethiol, 2-mercaptopropinic acid, thioglycolic acid, thiolactic acid, or other hydroxymercaptanes, aminomercaptans, or carboxyl-containing mercaptanes) and optionally other vinylic monomer are copolymerized (thermally or actinically) with a reactive vinylic monomer (having an amino or carboxyl group), in the presence of an free-radical initiator. Generally, the molar ratio of chain transfer agent to that of all of vinylic monomers other than the reactive vinylic monomer is from about 1:5 to about 1:100, whereas the molar ratio of chain transfer agent to the reactive vinylic monomer is 1:1. In such preparation, the chain transfer agent with amino or carboxyl group is used to control the molecular weight of the resultant hydrophilic polymer and forms a terminal end of the resultant hydrophilic polymer so as to provide the resultant hydrophilic polymer with one terminal amino or carboxyl group, while the reactive vinylic monomer provides the other terminal carboxyl or amino group to the resultant hydrophilic polymer. Similarly, to prepare a monoamino- or monocarboxyl-terminated homo- or co-polymer of a non-reactive hydrophilic vinylic monomer, the non-reactive vinylic monomer, a chain transfer agent with an amino or carboxyl group (e.g., 2-aminoethanethiol, 2-mercaptopropinic acid, thioglycolic acid, thiolactic acid, or other hydroxymercaptanes, aminomercaptans, or carboxyl-containing mercaptanes) and optionally other vinylic monomers are copolymerized (thermally or actinically) in the absence of any reactive vinylic monomer.

As used in this application, a copolymer of a non-reactive hydrophilic vinylic monomer refers to a polymerization product of a non-reactive hydrophilic vinylic monomer with one or more additional vinylic monomers. Copolymers comprising a non-reactive hydrophilic vinylic monomer and a reactive vinylic monomer (e.g., a carboxyl-containing vinylic monomer) can be prepared according to any well-known radical polymerization methods or obtained from commercial suppliers. Copolymers containing methacryloyloxyethyl phosphorylcholine and carboxyl-containing vinylic monomer can be obtained from NOP Corporation (e.g., LIPIDURE®-A and -AF).

The weight average molecular weight $M_w$ of the hydrophilic polymer having at least one amino, carboxyl or thiol group (as a hydrophilicity-enhancing agent) is preferably from about 500 to about 1,000,000, more preferably from about 1,000 to about 500,000.

Polyaminoamide-epichlorohydrin (PAE) (or polyamide-polyamine-epichlorohydrin or polyamide-epichlorohydrin) are commericially available, such as, for example, Kymene® or Polycup® resins (epichlorohydrin-functionalized adipic acid-diethylenetriamine copolymers) from Hercules or Polycup® or Servamine® resins from Servo/Delden. Alternatively, PAE can be obtained by reacting epichlorohydrin with a poly(amidoamine) which is a polycondensate derived from a polyamine and a dicarboxylic acid (e.g., adipic acid-diethylenetriamine copolymers). The reaction conditions for epichlorohydrin-functionalization of a polyamidoamine polymer are taught in EP1465931 (herein incorporated by reference in its entirety).

In accordance with the invention, the reaction between a hydrophilicity-enhancing agent and an azetidinium-containing copolymer of the invention (or polyamidoamine-epichlorohydrin) is carried out at a temperature of from about 40° C. to about 100° C. for a period of time sufficient (from about 0.3 hour to about 24 hours, preferably from about 1 hour to about 12 hours, even more preferably from about 2 hours to about 8 hours) to form a water-soluble and thermally-crosslinkable hydrophilic polymeric material containing reactive functional groups (azetidinium, carboxyl, amino, and/or thiol groups).

In a preferred embodiment, the thermally-crosslinkable hydrophilic polymeric material is an azetidinium-copolymer of the invention which comprises: (1) up to about 50% (preferably from about 2.5% to about 40%, more preferably from about 5% to about 30%, even more preferably from about 7.5% to about 25%) by moles of azetidinium-containing monomeric units (derived from at least one azetidinium-containing vinylic monomer of formula (1) or (2) as defined above) and reactive monomeric units; and (2) at least about 50%, preferably at least about 60%, more preferably at least about 70%, even more preferably at least about 75% by moles of non-reactive hydrophilic monomeric units derived from at least one hydrophilic vinylic monomer selected from the group consisting of (meth)acrylamide, N,N-dimethyl (meth)acrylamide, N-vinylpyrrolidone, N,N,-dimethylaminoethyl (meth)acrylate, N,N-dimethylaminopropyl (meth) acrylamide, glycerol methacrylate, 3-acryloylamino-1-propanol, N-hydroxyethyl acrylamide, N-[tris(hydroxymethyl) methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, hydroxypropyl (meth)acrylate, $C_1$-$C_4$-alkoxy polyethylene glycol (meth)acrylate having a weight average molecular weight of up to 1500 Daltons, N-vinyl formamide, N-vinyl acetamide, N-vinyl isopropylamide, N-vinyl-N-methyl acetamide, allyl alcohol, vinyl alcohol (hydrolyzed form of vinyl acetate in the copolymer), a phosphorylcholine-containing vinylic monomer (including (meth)acryloyloxyethyl phosphorylcholine and those described in U.S. Pat. No. 5,461,433, herein incorporated by reference in its entirety), a sugar-containing vinylic monomer (e.g., erythritol (meth)acrylate, arabitol (meth)acrylate, mannitol (meth)acrylate, ducitol (meth)acrylate, fucitol (meth)acrylate, iditol (meth)acrylate, innositol (meth)acrylate, xylitol (meth)acrylate, sorbitol (meth)acrylate, glucose (meth)acrylate, fructose (meth)acrylate, galactose (meth)acrylate), and combinations thereof.

In accordance with this aspect of the invention, the step of heating is performed preferably by autoclaving the silicone hydrogel contact lens immersed in a packaging solution (i.e., a buffered aqueous solution) in a sealed lens package at a temperature of from about 118° C. to about 125° C. for approximately 20-90 minutes. In accordance with this embodiment of the invention, the packaging solution is a buffered aqueous solution which is ophthalmically safe after autoclave.

Lens packages (or containers) are well known to a person skilled in the art for autoclaving and storing a soft contact lens. Any lens packages can be used in the invention. Preferably, a lens package is a blister package which comprises a base and a cover, wherein the cover is detachably sealed to the base, wherein the base includes a cavity for receiving a sterile packaging solution and the contact lens.

Lenses are packaged in individual packages, sealed, and sterilized (e.g., by autoclave at about 120° C. or higher for at least 30 minutes under pressure) prior to dispensing to users. A person skilled in the art will understand well how to seal and sterilize lens packages.

In accordance with the invention, a packaging solution contains at least one buffering agent and one or more other ingredients known to a person skilled in the art. Examples of other ingredients include without limitation, tonicity agents, surfactants, antibacterial agents, preservatives, and lubricants (e.g., cellulose derivatives, polyvinyl alcohol, polyvinyl pyrrolidone).

The packaging solution contains a buffering agent in an amount sufficient to maintain a pH of the packaging solution in the desired range, for example, preferably in a physiologically acceptable range of about 6 to about 8.5. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (2-amino-2-hydroxymethyl-1,3-propanediol), Bis-Tris (Bis-(2-hydroxyethyl)-imino-tris-(hydroxymethyl)-methane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N'-bis(2-ethanesulfonic acid), TES (N-[Tris (hydroxymethyl)methyl]-2-aminoethanesulfonic acid), salts thereof, phosphate buffers, e.g. $Na_2HPO_4$, $NaH_2PO_4$, and $KH_2PO_4$ or mixtures thereof. A preferred bis-aminopolyol is 1,3-bis(tris[hydroxymethyl]-methylamino)propane (bis-TRIS-propane). The amount of each buffer agent in a packaging solution is preferably from 0.001% to 2%, preferably from 0.01% to 1%; most preferably from about 0.05% to about 0.30% by weight.

The packaging solution has a tonicity of from about 200 to about 450 milliosmol (mOsm), preferably from about 250 to about 350 mOsm. The tonicity of a packaging solution can be adjusted by adding organic or inorganic substances which affect the tonicity. Suitable occularly acceptable tonicity agents include, but are not limited to sodium chloride, potassium chloride, glycerol, propylene glycol, polyols, mannitols, sorbitol, xylitol and mixtures thereof.

A packaging solution of the invention has a viscosity of from about 1 centipoise to about 8 centipoises, more preferably from about 1.5 centipoises to about 5 centipoises, at 25° C.

In a preferred embodiment, the packaging solution comprises preferably from about 0.01% to about 2%, more preferably from about 0.05% to about 1.5%, even more preferably from about 0.1% to about 1%, most preferably from about 0.2% to about 0.5%, by weight of a thermally-crosslinkable hydrophilic polymeric material of the invention.

In another preferred embodiment, a method of the invention can further comprise, before the step of heating, the steps of: contacting at room temperature the silicone hydrogel contact lens with an aqueous solution of the thermally-crosslinkable hydrophilic polymeric material to form a top layer (i.e., an LbL coating) of the thermally-crosslinkable hydrophilic polymeric material on the surface of the silicone hydrogel contact lens, immersing the silicone hydrogel contact lens with the top layer of the thermally-crosslinkable hydrophilic polymeric material in a packaging solution in a lens package; sealing the lens package; and autoclaving the lens package with the silicone hydrogel contact lens therein to form a crosslinked hydrophilic coating on the silicone hydrogel contact lens. Because of being positively charged, the thermally-crosslinkable hydrophilic polymeric material is believed to be capable of forming, on the prime coating of a silicone hydrogel contact lens, a non-covalently-bound layer through physical interactions.

A silicone hydrogel contact lens obtained according a method of the invention has a surface hydrophilicity/wettability characterized by having an averaged water contact angle of preferably about 90 degrees or less, more preferably about 80 degrees or less, even more preferably about 70 degrees or less, most preferably about 60 degrees or less.

All of the various embodiments including preferred embodiments of an azetidinium-containing vinylic monomer are described above and can be used in this aspect of the invention.

It should be understood that although various embodiments including preferred embodiments of the invention may be separately described above, they can be combined and/or used together in any desirable fashion in this aspect of the invention.

The invention, in another further aspect, provides a method for producing silicone hydrogel contact lenses each having a crosslinked hydrophilic coating thereon, the method of invention comprising the steps of: (a) obtaining a silicone hydrogel contact lens from a lens-forming composition comprising an azetidinium-containing copolymer (as described above) and/or an azetidinium-containing vinylic monomer of formula (1) or (2) as defined above; (b) heating the silicone hydrogel contact lens in an aqueous solution in the presence of a water-soluble, thermally-crosslinkable hydrophilic polymeric material comprising reactive groups selected from the group consisting of azetidinium groups, carboxyl groups, amino groups, thiol groups and combinations thereof, to and at a temperature from about 40° C. to about 140° C. for a period of time sufficient to induce intermolecular and intramolecular crosslinking reactions between one azetidinium group and one amino or carboxyl group, thereby forming a durable non-silicone hydrogel coating on the silicone hydrogel contact lens, wherein the non-silicone hydrogel coating is anchored onto the silicone hydrogel contact lens through the azetidinium groups of the azetidinium-containing copolymer on and/or near the surface of the silicone hydrogel contact lens.

It is believed that a portion of the azetidinium-containing copolymer and/or azetidinium-containing monomeric units may be located on and/or near the surface of the silicone hydrogel contact lens obtained from the lens-forming composition comprising the azetidinium-containing copolymer. Those azetidinium groups on and/or near the lens surface can serve as anchoring sites for attaching the non-silicone hydrogel coating.

In a preferred embodiment, the azetidinium-containing copolymer is compatible with polymerizable components in the lens-forming composition and comprises azetidinium-containing monomeric units derived from an azetidinium-containing vinylic monomer of formula (1) or (2) as defined above and hydrophobic monomeric units derived from a hydrophobic vinylic monomer. More preferably, the azetidinium-containing copolymer is substantially free (preferably free of) of any ethylenically unsaturated group.

The term "compatible with polymerizable components in the lens-forming composition" in reference to an azetidinium-containing copolymer means that the lens-forming composition comprising the azetidinium-containing copolymer and the polymerizable components has an optical transmissibility (between 400 nm to 700 nm) of at least about 85%, more preferably at least about 90%, even more preferably at least about 95%, most preferably at least about 98%.

In a preferred embodiment, the method further comprises a step of applying a prime coating of an anchoring polymer onto the silicone hydrogel contact lens. All the embodiments (including preferred embodiments) of anchoring polymers described above can be used in this preferred embodiment of the method of the invention in this aspect.

Preferably, the step of heating is performed by autoclaving the silicone hydrogel contact lens immersed in a packaging solution (i.e., a buffered aqueous solution) in a sealed lens package at a temperature of from about 118° C. to about 125° C. for approximately 20-90 minutes.

Preferably, the packaging solution comprises from about 0.01% to about 2%, preferably from about 0.05% to about 1.5%, more preferably from about 0.1% to about 1%, even more preferably from about 0.2% to about 0.5%, by weight of the thermally-crosslinkable hydrophilic polymeric material.

All of the various embodiments including preferred embodiments of a silicone hydrogel contact lens, a SiHy lens formulation, an azetidinium-containing vinylic monomer, an anchoring polymer and its uses for forming a prime coating, a water-soluble, thermally-crosslinkable hydrophilic polymeric material, the step of heating the silicone hydrogel contact lens in an aqueous solution in the presence of a water-soluble, thermally-crosslinkable hydrophilic polymeric material, a lens packaging solution and components thereof, lens packages, are described above and can be combined and/or used together in this aspect of the invention.

In still a further aspect, the invention provides a silicone hydrogel contact lens comprising a lens body made of a silicone hydrogel material and a non-silicone hydrogel coating thereon, wherein the non-silicone hydrogel coating is obtained by thermally inducing intermolecular and intramolecular crosslinking of a thermally-crosslinkable hydrophilic polymeric material which comprises azetidinium-containing monomeric units derived from at least one azetidinium-containing vinylic monomer (preferably a monomer of formula (1) or (2) described above) and reactive monomeric units derived from a vinylic monomer having an amino or carboxyl group, wherein the silicone hydrogel contact lens has an oxygen permeability of at least about 40 barrers, a surface wettability characterized by a water contact angle of about 100 degrees or less, and a good coating durability characterized by surviving a digital rubbing test.

In accordance with the invention, a lens body refers of a preformed silicone hydrogel contact lens to be coated and is obtained from a silicone hydrogel lens formulation (composition) as described above.

In a preferred embodiment, the silicone hydrogel contact lens has at least one property selected from the group consisting of: an oxygen permeability of at least about 50 barrers, preferably at least about 60 barrers, more preferably at least about 70 barrers; an elastic modulus of about 1.5 MPa or less, preferably about 1.2 MPa or less, more preferably about 1.0 or less, even more preferably from about 0.3 MPa to about 1.0 MPa; a water content of preferably from about 18% to about 70%, more preferably from about 20% to about 60% by weight when fully hydrated; and combination thereof.

Various embodiments including preferred embodiments of a silicone hydrogel contact lens to be coated, azetidinium-containing vinylic monomer, and a thermally-crosslinkable hydrophilic polymeric material are described above and can be combined and/or used together in this aspect of the invention.

The water content of a silicone hydrogel contact lens can be measured according to Bulk Technique as disclosed in U.S. Pat. No. 5,849,811.

In still another further aspect, the invention provides an ophthalmic product, which comprises a sterilized and sealed lens package, wherein the lens package comprises: a post-autoclave lens packaging solution and a readily-usable silicone hydrogel contact lens immersed therein, wherein the readily-usable silicone hydrogel contact lens comprises a crosslinked hydrophilic coating obtained by autoclaving an original silicone hydrogel contact lens having amino groups and/or carboxyl groups on and/or near the surface of the original silicone hydrogel contact lens in a pre-autoclave packaging solution containing a water-soluble and thermally-crosslinkable hydrophilic polymeric material which comprises from 0.001% to about 25% by mole of azetidinium-containing monomeric units derived from at least one azetidinium-containing vinylic monomer, wherein the hydrophilic polymeric material is covalently attached onto the silicone hydrogel contact lens through second covalent linkages each formed between one amino or carboxyl group on and/or near the surface of the silicone hydrogel contact lens and one azetidinium group of the hydrophilic polymeric material, wherein the post-autoclave packaging solution comprises at least one buffering agent in an amount sufficient to maintain a pH of from about 6.0 to about 8.5 and an hydrolyzed product of the hydrophilic polymeric material and has a tonicity of from about 200 to about 450 milliosmol (mOsm) and a viscosity of from about 1 centipoise to about 10 centipoises.

All of the various embodiments including preferred embodiments of a silicone hydrogel contact lens, a SiHy lens formulation, an azetidinium-containing vinylic monomer, an anchoring polymer and its uses for forming a prime coating, a water-soluble, thermally-crosslinkable hydrophilic polymeric material, the step of heating the silicone hydrogel contact lens in an aqueous solution in the presence of a water-soluble, thermally-crosslinkable hydrophilic polymeric material, a lens packaging solution and components thereof, lens packages, are described above and can be combined and/or used together in this aspect of the invention.

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together. Therefore, the spirit and scope of the appended claims should not be limited to the description of the preferred versions contained therein.

Example 1

Oxygen Permeability Measurements

The apparent oxygen permeability ($Dk_{app}$), the apparent oxygen transmissibility (Dk/t), the intrinsic (or edge-corrected) oxygen permeability ($Dk_c$) of a lens and a lens material are determined according to procedures described in Example 1 of U.S. patent application publication No. 2012/0026457 A1 (herein incorporated by reference in its entirety).

Lubricity Evaluation

The lubricity rating is a qualitative ranking scheme where 0 is assigned to control lenses coated with polyacrylic acid (PAA), 1 is assigned to Oasys™/TruEye™ commercial lenses and 5 is assigned to commercial Air Optix™ lenses. The samples are rinsed with excess DI water for at least three times and then transferred to PBS before the evaluation. Before the evaluation, hands are rinsed with a soap solution, extensively rinsed with DI water and then dried with KimWipe® towels. The samples are handled between the fingers and a numerical number is assigned for each sample relative to the above standard lenses described above. For example, if lenses are determined to be only slightly better than Air Optix™ lenses, then they are assigned a number 4. For consistency, all ratings are independently collected by the same two operators in order to avoid bias and the data so far reveal very good qualitative agreement and consistency in the evaluation.

Surface Hydrophilicity/Wetability Tests.

Water contact angle on a contact lens is a general measure of the surface hydrophilicity (or wetability) of the contact lens. In particular, a low water contact angle corresponds to more hydrophilic surface. Average contact angles (Sessile Drop) of contact lenses are measured using a VCA 2500 XE contact angle measurement device from AST, Inc., located in Boston, Mass. This equipment is capable of measuring advancing or receding contact angles or sessile (static) contact angles. The measurements are performed on fully hydrated contact lenses and immediately after blot-drying as follows. A contact lens is removed from the vial and washed 3 times in ~200 ml of fresh DI water in order to remove loosely bound packaging additives from the lens surface. The lens is then placed on top of a lint-free clean cloth (Alpha Wipe TX1009), dabbed well to remove surface water, mounted on the contact angle measurement pedestal, blown dry with a blast of dry air and finally the sessile drop contact angle is automatically measured using the software provided by the manufacturer. The DI water used for measuring the contact angle has a resistivity>18MΩcm and the droplet volume used is 2 µl. Typically, uncoated silicone hydrogel lenses (after autoclave) have a sessile drop contact angle around 120 degrees. The tweezers and the pedestal are washed well with Isopropanol and rinsed with DI water before coming in contact with the contact lenses.

Water Break-Up Time (WBUT) Tests.

The wettability of the lenses (after autoclave) is also assessed by determining the time required for the water film to start breaking on the lens surface. Briefly, lenses are removed from the vial and washed 3 times in 200 ml of fresh DI water in order to remove loosely bound packaging additives from the lens surface. The lens is removed from the solution and held against a bright light source. The time that is needed for the water film to break (de-wet) exposing the underlying lens material is noted visually. Uncoated lenses typically instantly break upon removal from DI water and are assigned a WBUT of 0 seconds. Lenses exhibiting WBUT≥5 seconds are considered wettable and are expected to exhibit adequate wettability (ability to support the tear film) on-eye.

Coating Intactness Tests.

The intactness of a coating on the surface of a contact lens can be tested according to Sudan Black stain test as follow. Contact lenses with a coating (an LbL coating, a plasma coating, or any other coatings) are dipped into a Sudan Black dye solution (Sudan Black in vitamin E oil). Sudan Black dye is hydrophobic and has a great tendency to be adsorbed by a hydrophobic material or onto a hydrophobic lens surface or hydrophobic spots on a partially coated surface of a hydrophobic lens (e.g., silicone hydrogel contact lens). If the coating on a hydrophobic lens is intact, no staining spots should be observed on or in the lens. All of the lenses under test are fully hydrated.

Tests of Coating Durability.

The lenses are digitally rubbed (wearing disposable powder-free latex gloves) with Solo-Care® multi-purpose lens care solution for 30 times and then rinsed with saline. The above procedure is repeated for a given times, e.g., from 1 to 30 times, (i.e., number of consecutive digital rubbing tests which imitate cleaning and soaking cycles). The lenses are then subjected to Sudan Black test (i.e., coating intactness test described above) to examine whether the coating is still intact. To survive digital rubbing test, there is no significantly increased staining spots (e.g., staining spots covering no more than about 5% of the total lens surface). Water contact angles are measured to determine the coating durability.

Tests of Lenses with Contact Lens Analyzer at Low pH (Low pH CLAN).

Low pH CLAN tests for the coating coverage on lens surfaces using a hydrophobic (Nile red, also known as Nile Blue Oxazone) dye. Any exposed hydrophobic areas on the lens will bind hydrophobic dye. If a homogeneous coating on the lens is intact, no staining spots should be observed on or in the lens. The test is done by dipping a contact lens into 1N HCl(aq) for about 30 seconds, followed by a 2 second dip in a Nile red solution (1-propanol/n-Heptane), and finally a 30 second dip in DI water to rinse off the excess dye. The lens is then placed in the CLAN (digital camera at a fixed focus through a magnifying optics and filter) where the lens is then illuminated with the blue fluorescence excitation light. The image is captured and analyzed by image processing software for the hydrophobic fluorescence dye adsorbed by the hydrophobic surfaces. The lens is considered a failure if the sum of half the number of light pixels and half the number of dark pixels is greater than 5000.

Bead Testing.

Bead testing is used to determine the negative charge on the contact lens surface. A bead testing value of 50 or less is acceptable for the charge on the lens surface. Higher values also reflect if the packaged coating is not able to cover a PAA/PMAA coated lens which generally has bead numbers>200. In this method, 0.2 g of Dovex 1×4 chloride form 50-100 mesh (CAS 69011-19-4) is measured in a centrifuge cup followed by addition of 4 ml PBS (phosphate buffered saline). A lens is placed on the back side of the tube and the tube is shaken for 1 min at 300 rpm. After this, the tube is rinsed and replaced with 5 ml of PBS followed by shaking for 1 min at 300 rpm to get rid of any superficial beads. The lens is than analyzed under a microscope and beads are counted.

TBO Assay.

Prepare a stock solution of sodium phosphate dibasic (0.2% wt/wt, pH 2). Prepare a stock solution of sodium bicarbonate (0.2% wt/wt, pH 10). Prepare a stock solution of Toluidine Blue O (abbreviated TBO, 2000 ppm) in water. Set two digital block heaters to 35 and 50° C. Prepare freshly diluted 0.1% (wt/wt) solutions of both the pH 2 and pH 10 buffers. Prepare 50 ppm TBO solution from the TBO stock solution (2000 ppm). Rinse each lens to be tested in 100 mL of DI water for about 5 minutes. Blot each lens to remove excess water using Alpha wipe synthetic wipers. Place the lenses in a 24-well TCPS plate (one lens per well). Pipette in 1.5 ml of the 50 ppm stain solution into each well and place the plate on the heating block at 50° C. for 30 minutes. After the above staining step is complete, remove the lenses and place them in new wells of a 24-well TCPS plate. Pipette in fresh 1.5 ml of 0.1% pH 10 buffer solution and the leave the lenses at room temperature for 5 min. After the above rinse step is complete, remove the lenses and place them in new wells of a 24-well TCPS plate. Pipette in fresh 1.5 ml of 0.1% pH 10 buffer solution. Leave the plate on the block heater set at 35° C. for 30 min. Remove the lenses from the wells and gently blot away the excess stain using the Alpha wipe synthetic wipers. Place the lenses into wells of a new 24-well TCPS plate and pipette in 1.5 ml of 0.1% pH 2 solution. Leave the plate on the block heater set at 50° C. for 30 min. The bound dye is released from the lenses during this step. Remove the lens from the well. The solutions will be used for UV-VIS analysis and quantification. Prepare calibration standards of 0 to 100 ppm of TBO in 0.1% pH 2 solution. Measure the spectrum of the standard TBO solutions, the unknown solutions from the coated lenses, and the solutions from an uncoated lens at wavelengths 625, 630, and 635. Substract the absorbance values from the uncoated lens solutions from the coated lens solutions then use the calibration curve to determine the amount of TBO.

PHMB Method.

Prepare 1 liter of phosphate buffered saline (PBS) by dissolving 7.85 g NaCl, 0.773 g monobasic sodium phosphate, and 4.759 g dibasic sodium phosphate in purified water. Adjust pH to 7.1 to 7.3 as needed. Prepare ATS solution by combining 4.500 grams NaCl, 0.074 g calcium chloride dihydrate, 0.550 g citric acid monohydrate, 1.400 g sodium citrate, and 493.475 g purified water. Adjust to pH 7.0. Prepare 10 ppm PHMB solution in PBS. Place each lens into 3 mL of the 10 ppm PHMB solution overnight (>16 hours). Remove lenses then blot to remove excess PBS solution. Place 2 blotted lenses into 2 mL of ATS solution. Agitate using an orbital shaker at 250 rpm for 2 hours. After 2 hours carefully remove the lenses from solution to minimize solution loss. Prepare PHMB standard solutions in PBS (0.5, 1, 2, 4, 8, and 10 ppm). Using a 1 cm quartz cell, measure the absorbance at 240 nm for the standard, uptake and release samples to determine the concentration of PHMB.

Example 2

Synthesis of Diethyl Azetidinium Methacrylate Ester Chloride Salt (AZM) Monomer 2a. Synthesis of Diethyl Hydroxyl Azetidinium Chloride.

Diethyl amine (50 g, 0.686 mole) is dissolved in 25 mL of dry acetonitrile under argon. The solution is cooled down in an ice bath to 0° C. To this solution, epichlorohydrin (63.248 g, 0.684 mole) in 20 mL of dry acetonitrile is added. After the mixture is stirred at 0° C. for about 5 hours, the reaction is then performed at room temperature for another about 27 hours. The solid product is collected by filtration and washed with cold acetonitrile for a couple times. The typical yield is in the range from 30-50%.

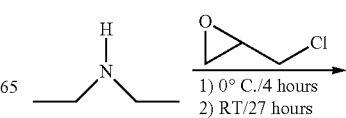

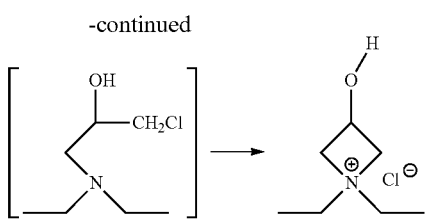

2b: Synthesis of Diethyl Azetidinium Methacrylate Ester Chloride Salt (AZM).

In a Schlenk flask equipped with nitrogen flow, the obtained hydroxy azetidinium chloride salt (60 g, 0.362 mole) is dissolved in 336 mL of dry acetonitrile. To this solution, methacrylic acid anhydride (45.73 g, 0.297 mole) and di-tert-butyl-4-methylphenol (7 mg) are added over about 5 minutes at room temperature. The reaction mixture is then stirred at room temperature for about 18 hours. The acetonitrile is evaporated and the residual is suspended in 1 L of acetonitrile/diethyl ether (1:1) solvent mixture. The solid product is collected by filtration and dried. The typical yield is around 55%

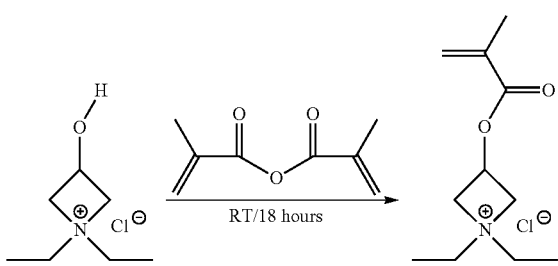

Example 3

Synthesis of in-Package Coating (IPC) Copolymers

3a. Preparation of AZM/APMA/PEG/DMA Containing Copolymer for IPC.

In a 500 mL glass reaction kettle, 5.0 grams of a solution of methoxy polyethylene glycol 2000 methacrylate (PEG2000-MA) (50% in water), 1.0 gram of aminopropylmethacrylamide (APMA), 1.0 gram of AZM prepared in Example 2, 5.47 grams of N,N'-dimethylacrylamide (DMA), and 3.00 mL of Irgacure 2959 solution (1% in water) are dissolved in 184.53 grams of 33.75 mM citrate buffer (pH 4). A lid is put onto the reaction kettle that contains at least 4 ground glass joints. One used for a glass stir shaft, one for a thermocouple, one for a nitrogen inlet, and one for sampling access. The solution is sparged with nitrogen for 20 minutes at about 200 mL/min. The nitrogen flow rate is reduced to about 150 mL/min. The stir speed is set to 150 rpm. The reaction kettle is put into a Rayonet UV reactor with RPR-3500 UV bulbs. Four UV bulbs are turned on for about 1 hour at an intensity of about 2.0 mW/cm². After about one hour, the solution is vacuum filtered through qualitative filter paper. The copolymer solution is then purified using 50 kDa dialysis membranes against water for 24 hours using a water flow rate of about 40 mL/min. The solids content is determined and diluted to 2% if necessary.

3b. Preparation of AZM/APMA/Acrylamide Containing Copolymer for IPC.

In a 500 mL glass reaction kettle, 1.5 grams of aminopropylmethacrylamide (APMA), 1.5 grams of AZM prepared in Example 2, 6.97 grams of acrylamide, and 3.00 mL of Irgacure 2959 solution (1% in water) are dissolved in 187.03 grams of 33.75 mM citrate buffer (pH 4). A lid is put onto the reaction kettle that contains at least 4 ground glass joints, one used for a glass stir shaft, one for a thermocouple, one for a nitrogen inlet, and one for sampling access. The solution is sparged with nitrogen for 20 minutes at about 200 mL/min. The nitrogen flow rate is reduced to about 150 mL/min. The stir speed is set to 150 rpm. The reaction kettle is put into a Rayonet UV reactor with RPR-3500 UV bulbs. Four UV bulbs are turned on for 1 hour at an intensity of about 2.0 mW/cm². After 1 hour, the solution is vacuum filtered through qualitative filter paper. The copolymer solution is then purified using 50 kDa dialysis membranes against water for 24 hours using a flow rate of about 40 mL/min. The solids content is determined and diluted to 2% if necessary.

3c. Preparation of AZM/APMA/PEG/AGA Containing Copolymer for IPC.

In a 500 mL glass reaction kettle, 5.0 grams of a 50% PEG2000-MA solution in water, 1.0 grams of aminopropylmethacrylamide (APMA), 1.0 grams of AZM prepared in Example 2, 5.47 grams of acryloyl glucosamine (AGA), and 3.00 mL of a 1% Irgacure 2959 solution in water are dissolved in 184.53 grams of 33.75 mM citrate buffer (pH 4). A lid is put onto the reaction kettle that contains at least 4 ground glass joints, one used for a glass stir shaft, one for a thermocouple, one for a nitrogen inlet, and one for sampling access. The solution is sparged with nitrogen for 20 minutes at about 200 mL/min. The nitrogen flow rate is reduced to about 150 mL/min. The stir speed is set to 150 rpm. The reaction kettle is put into a Rayonet UV reactor with RPR-3500 UV bulbs. Four UV bulbs are turned on for 1 hour at an intensity of about 2.0 mW/cm². After about one hour, the solution is vacuum filtered through qualitative filter paper. The copolymer solution is then purified using 50 kDa dialysis membranes against water for 24 hours. The solids content is determined and diluted to 2% if necessary.

3d. Preparation of AZM/APMA/AA/Acrylamide Containing Copolymers for IPC.

In a 500 mL glass reaction kettle, 1.5 grams of aminopropylmethacrylamide (APMA), 1.5 grams of AZM prepared in Example 2, 0.2 grams of acrylic acid, 6.77 grams of acrylamide, and 3.00 mL of a 1% Irgacure 2959 solution in water are dissolved in 187.03 grams of 33.75 mM citrate buffer (pH 4). A lid is put onto the reaction kettle that contains at least 4 ground glass joints, one used for a glass stir shaft, one for a thermocouple, one for a nitrogen inlet, and one for sampling access. The solution is sparged with nitrogen for 20 minutes at about 200 mL/min. The nitrogen flow rate is reduced to about 150 mL/min. The stir speed is set to 150 rpm. The reaction kettle is put into a Rayonet UV reactor with RPR-3500 UV bulbs. Four UV bulbs are turned on for about one hour at an intensity of about 2.0 mW/cm². After about one hour, the solution is vacuum filtered through qualitative filter paper. The copolymer solution is then purified using 50 kDa dialysis membranes against water for 24 hours using a flow rate of about 40 mL/min. The solids content is determined and diluted to 2% if necessary.

Example 4

Synthesis of Amphiphilic Copolymers (ACP)

4a. Preparation of AZM/AA/PDMS/DMA Containing Copolymers.

In a 1 L glass reaction kettle 6.0 grams of monomethacryloxypropyl terminated polydimethylsiloxane (Gelest catalog # MCR-M11) (PDMS$_{1000}$-MA) is added. A lid is put onto the reaction kettle that contains at 4 ground glass joints, one used for a glass stir shaft, one for a thermocouple, one for vacuum and nitrogen inlet, one for a 200 mL pressure equalizing addition funnel, and one for sampling access. A 2 mbar vacuum is pulled to degas the PDMS$_{1000}$-MA for 10 minutes. After about 10 minutes, reaction kettle is filled with nitrogen. This degassing and nitrogen-filing procedure is repeated 6 times. In the 200 mL pressure equalizing addition funnel, 3.0 grams of AZM prepared in Example 2, 6.0 grams of acrylic acid (AA), 14.91 grams of DMA, and 3.00 mL of a 1% Irgacure 2959 solution in t-amyl alcohol are dissolved in 100.3 grams of t-amyl alcohol and 33.3 grams of methanol. A 100 mbar vacuum is pulled on the solution in the addition funnel for about 10 minutes. After about 10 minutes the funnel is filled with nitrogen. This degassing and nitrogen-filling procedure is repeated 3 times. After both PDMS$_{1000}$-MA and solution have been degassed, add the solution to the kettle with the PDMS$_{1000}$-MA. The stir speed is set to 150 rpm. The reaction kettle is put into a Rayonet UV reactor with RPR-3500 UV bulbs. Two UV bulbs are turned on for about one hour at an intensity of about 2.0 mW/cm$^2$. The copolymer solution is then purified using 25 kDa dialysis membranes against 1-PrOH for about 35 hours including two changes of 1-PrOH (1-propanol) during that time. The solids content is determined and diluted to 10% if necessary.

4b. Preparation of AZM/AA/Bulky TRIS/DMA Containing Copolymer.

The procedure is the same as 4a except 6.0 grams of bulky TRIS (Gelest catalog # MCT-M11) is used instead of PDMS$_{1000}$-MA.

4c. Preparation of AZM/AA/POSS-MA/DMA Containing Copolymer.

In a 1 L glass reaction kettle 6.0 grams of methacryllsobutyl POSS® (Hybrid Plastics catalog # MA0702, CAS #307531-94-8) (hereinafter "POSS-MA), 3.0 grams of AZM prepared in Example 2, 6.0 grams of acrylic acid (AA), 14.91 grams of DMA, 3.00 mL of a 1% Irgacure 2959 solution in t-amyl alcohol, 100.3 grams of t-amyl alcohol, and 33.5 g of methanol are added. The solution is sparged with nitrogen for 20 minutes at about 200 mL/min. The nitrogen flow rate is reduced to about 150 mL/min. The stir speed is set to 150 rpm. The reaction kettle is put into a Rayonet UV reactor with RPR-3500 UV bulbs. Two UV bulbs are turned on for 45 minutes. The copolymer solution is then purified using 25 kDa dialysis membranes against 1-PrOH for about 35 hours. The solids content is determined and diluted to 10% if necessary.

4d. Preparation of AZM/AA/TRIS/DMA or Containing Copolymer.

The procedure is the same as 4c except 6.0 grams of TRIS is used instead of or 6.0 grams of POSS-MA.

4e. Preparation of AZM/AA/PDMS/DMA Containing Copolymers.

In a 1 L glass reaction kettle 3.0 grams of monomethacryloxypropyl terminated polydimethylsiloxane (Gelest catalog # MCR-M11) (PDMS$_{1000}$-MA) is added. A lid is put onto the reaction kettle that contains at 4 ground glass joints, one used for a glass stir shaft, one for a thermocouple, one for vacuum and nitrogen inlet, one for a 200 mL pressure equalizing addition funnel, and one for sampling access. A 2 mbar vacuum is pulled to degas the PDMS$_{1000}$-MA for 10 minutes. After about 10 minutes, reaction kettle is filled with nitrogen. This degassing and nitrogen-filing procedure is repeated 6 times. In the 200 mL pressure equalizing addition funnel, 3.0 grams of AZM prepared in Example 2, 12.0 grams of acrylic acid (AA), 11.91 grams of DMA, and 3.00 mL of a 1% Irgacure 2959 solution in t-amyl alcohol are dissolved in 67 grams of t-amyl alcohol and 67 grams of methanol. A 175 mbar vacuum is pulled on the solution in the addition funnel for about 10 minutes. After about 10 minutes the funnel is filled with nitrogen. This degassing and nitrogen-filling procedure is repeated 3 times. After both PDMS$_{1000}$-MA and solution have been degassed, add the solution to the kettle with the PDMS$_{1000}$-MA. The stir speed is set to 150 rpm. The reaction kettle is put into a Rayonet UV reactor with RPR-3500 UV bulbs. Two UV bulbs are turned on for about one hour at an intensity of about 2.0 mW/cm$^2$. The copolymer solution is then purified using 25 kDa dialysis membranes against 1-PrOH for about 35 hours including two changes of 1-PrOH (1-propanol) during that time. The solids content is determined and diluted to 10% if necessary.

Example 5

Preparation of Phosphate/Citrate Buffer Concentrate.

The buffer concentrate is prepared by dissolving 0.484% by weight of sodium citrate dihydrate, 0.708% by weight of sodium phosphate dibasic, 0.088% by weight of sodium phosphate monobasic, monohydrate, and 1.486% by weight of sodium chloride in DI water. The pH is adjusted to about 7.2, if necessary.

Preparation of IPC Saline Solutions with AZM-Containing Copolymers.

In-package coating solutions (IPC-5A to IPC-5D) are prepared from 2% AZM-containing copolymer solutions (3a-3d of Example 3) and the buffer concentrate prepared above and have the compositions shown in the table below. The pH of IPC-5A to IPC-5D is adjusted, if necessary, to pH 7.2 to 7.4.

| IPC Saline ID | AZM-containing Copolymer Concentration | Example # | PBS concentrate (g) | Water (g) |
|---|---|---|---|---|
| 5A | 1% (w/w) | 3a (9 grams) | 9 | — |
| 5B | 1% (w/w) | 3b (9 grams) | 9 | — |
| 5C | 1% (w/w)1 | 3c (9 grams) | 9 | — |
| 5D | 0.5% (w/w) | 3d (4.5 grams) | 9 | 4.5 |

Preparation of IPC-5E.

Poly(AAm-co-AA)(90/10) partial sodium salt (~90% solid content, poly(AAm-co-AA) 90/10, Mw 200,000) is purchased from Polysciences, Inc. and used as received. Polyamidonamine epichlorohydrin (PAE) (Kymene, an azetidinium content of 0.46 assayed with NMR) is purchased from Ashland as an aqueous solution and used as received. IPC-5E is prepared by dissolving about 0.07% w/w of poly(AAm-co-AA)(90/10) and about 0.15% of PAE (an initial azetidinium millimolar equivalents of about 8.8 millimole) in phosphate-buffered saline (PBS) (about 0.044 w/w % NaH$_2$PO$_4$.H$_2$O, about 0.388 w/w/% Na$_2$HPO$_4$.2H$_2$O, about 0.79 w/w % NaCl) and adjusting the pH to 7.2~7.4. Then the IPC-5E is heat pre-treated for about 6 hours at about 60° C. (heat pretreatment). During this heat pretreatment, poly(AAm-co-AA) and PAE are partially crosslinked to each other (i.e., not consuming all azetidinium groups of PAE) to form a water-soluble and thermally-crosslinkable hydrophilic polymeric material containing azetidinium groups within the branched polymer network in the IPC-5E. After the heat pre-treatment, the IPC-5E is cooled to room temperature then filtered using a 0.22 micron PES membrane filter.

Example 6

Silicone hydrogel contact lenses with a PAA coating thereon are prepared according to the procedures (the lens formulation, molds, cast-molding conditions, lens extraction, PAA coating solution, PAA coating procedures, etc.) described in Example 19 of U.S. patent application publication No. 2012/0026458 A1 (herein incorporated by reference in its entirety).

PAA-Coating Solution.

A polyacrylic acid (PAA) coating solution is prepared by dissolving an amount of PAA (M.W.: 450 kDa, from Lubrizol) in a given volume of 1-propanol (1-PrOH) to have a concentration of about 0.44% by weight and the pH is adjusted with formic acid to about 2.0.

Contact lenses with a PAA coating thereon are packaged in polypropylene lens packaging shells/blisters (one lens per shell) each containing 0.55 mL of one of the following packaging salines: phosphate-buffered saline (PBS) and IPC-5A to IPC-5D (prepared in Example 5). The blisters are then sealed with foil and autoclaved for about 30 minutes at 121° C. Crosslinked coatings are formed during the autoclave on those lenses immersed in a packaging saline containing an azetidinium-containing copolymer or polymeric material. Resultant lenses after autoclave are characterized and the results are reported in the table below.

|  | PBS | IPC-5A | IPC-5B | IPC-5C | IPC-5D |
|---|---|---|---|---|---|
| WBUT (s) | 10+ | 9 | 10 | 1 | 14 |
| Lubricity | 0 | 0.5 | 0.5 | 0.5 | 0.5 |
| Bead Test | >250 | 2 | 121 | 42 | 117 |
| Low pH CLAN | Pass | Pass | Pass | Pass | Pass |

Example 7

Preparation of Lenses.

Silicone hydrogel contact lenses are prepared by cast-molding according the procedures (the lens formulation, molds, cast-molding conditions, etc.) described in Example 19 of U.S. patent application publication No. 2012/0026458 A1 (herein incorporated by reference in its entirety).

PMAA-Coating Solutions.

A polymethacrylic acid (PMAA) solution is prepared by dissolving PMAA (Mn~418K) and formic acid in a given volume of a water/1-propanol mixture, and then diluted with water and 1-propanol to forming PMAA coating solutions having the following compositions:
1. 40×PMAA: PMAA (0.011% w/w); 1-propanol (86.19% w/w); water (9.63% w/w); and formic acid (3.74% w/w).
2. FS PMAA: PMAA (0.44% w/w); 1-propanol (86.63% w/w); water (9.63% w/w); and formic acid (3.74% w/w).

PMAA-Coated Lenses.

Cast-molded contact lenses obtained as above are extracted and coated by dipping in the following series of baths: DI water bath for about 56 seconds; 3 methyl ethyl ketone (MEK) baths for about 22, 78, 226 second respectively; one DI water bath for about 56 seconds; one bath of PMAA coating solution (prepared above) for about 100 seconds; one bath of a water/1-propanol 50%/50% mixture for about 56 seconds; one bath of water for about 56 seconds; one bath of phosphate buffered saline for about 56 seconds; and one DI water bath for about 56 seconds.

Application of Crosslinked Coating.

Contact lenses with a PMAA coating thereon are packaged in polypropylene lens packaging shells/blisters (one lens per shell) each containing 0.55 mL of one of the following packaging salines: PBS (as control), IPC-5A (prepared in Example 5), and IPC-5B (prepared in Example 5). The blisters are then sealed with foil and autoclaved for about 30 minutes at about 121° C. Crosslinked coatings are formed during the autoclave on those lenses immersed in a packaging saline containing an azetidinium-containing copolymer or polymeric material.

Characterization of SiHy Lenses.

Resultant lenses after autoclave are characterized and the results are reported in the table below.

| Packaging Saline | PBS | IPC-5A | IPC-5B |
|---|---|---|---|
| Contact angle (degrees) | 103 | 46 | 36 |
| WBUT (s) | NA | 3 | 6 |
| Lubricity | NA | 0.5 | 0.5 |

NA = data not collected

Example 8

This example illustrates preparation of an amphiphilic copolymer (ACP) that uses AZM (as prepared in Example 2) and acrylic acid to provide a cross-linkable primary coating designed to react with the IPC copolymer.

The structure of such a copolymer is shown below.

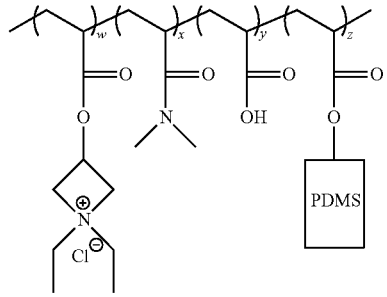

AZM is the electrophile and acrylic acid is the nucleophile in the copolymer. Both can react with a crosslinkable copolymer added to a saline solution to apply a in-package crosslinked coating on a silicone hydrogel contact lens. The copolymer also incorporates polydimethylsiloxane segment (PDMS) to provide a hydrophobic interaction to attach the copolymer to the surface of a hydrophobic lens (e.g., a silicone hydrogel contact lens). DMA is used to provide hydrophilicity and high molecular weight copolymers. The copolymer has much less acrylic acid content (concentration) compared to polyacrylic acid (PAA) or polymethacrylic acid (PMAA) homopolymers.

The preferred range of weight percentages of monomers used in a reaction mixture for preparing a copolymer of the invention is listed in table 1 below. The copolymer is prepared according to the procedure similar to that described in Example 4 for preparing Copolymer 4a.

|  | AZM | Acrylic Acid | PDMS | DMA |
|---|---|---|---|---|
| Range | 10-15% | 10-40% | 10-60% | Remaining % |

Preparation of Lenses.

Silicone hydrogel contact lenses are prepared by cast-molding according the procedures (the lens formulation, molds, cast-molding conditions, etc.) described in Example 19 of U.S. patent application publication No. 2012/0026458 A1 (herein incorporated by reference in its entirety).

Preparation of ACP Coating Solutions.

Amphiphilic copolymer solutions (herein after ACP coating solutions I to IV) each are prepared by dissolving one of ACP copolymers 4a to 4e (about 10% solution) prepared in Example 4 in a mixture of 1-propanol (85%) and water (15%). The ACP concentration is about 1% by weight.

ACP-Coated Lenses.

Cast-molded contact lenses as above are extracted and coated with ACP by dipping in the following series of baths: one DI water bath for about 56 seconds; 3 MEK baths for about 22, 78, and 224 second respectively; one DI water bath for about 56 seconds; one bath of ACP coating solution (about 1% by weight) in a mixture of 1-propanol/water (85%/15%) for about 180 seconds; one bath of a water/1-propanol (58%/42%) mixture for about 180 seconds; one bath of a water/1-propanol (72%/28%) mixture for about 180 seconds; and one DI water bath for about 180 seconds. ACP-I coated lenses are obtained using ACP coating solution I (containing ACP copolymer 4a); ACP-II coated lenses are obtained using ACP coating solution II (containing ACP copolymer 4b); ACP-III coated lenses are obtained using ACP coating solution II (containing ACP copolymer 4c); ACP-IV coated lenses are obtained using ACP coating solution IV (containing ACP copolymer 4d). Control A lenses are obtained according to the procedures above, except that bath 6 is free of ACP and contains only the solvent mixture.

Application of Crosslinked Coating.

ACP-coated contact lenses prepared above are packaged in polypropylene lens packaging shells/blisters (one lens per shell) each containing 0.55 mL of one of the following packaging salines: PBS (as control) and IPC-5E (prepared in Example 5). Control A lenses are packaged in polypropylene lens packaging shells/blisters (one lens per shell) each containing 0.55 mL of PBS. Control B lenses are ACP-coated lenses which are packaged in polypropylene lens packaging shells/blisters (one lens per shell) each containing 0.55 mL of PBS. The blisters are then sealed with foil and autoclaved for 30 minutes at about 121° C. Crosslinked coatings are formed during the autoclave on those lenses immersed in a packaging saline containing an azetidinium-containing copolymer or polymeric material.

Characterization of SiHy Lenses.

Resultant lenses after autoclave are characterized and the results are reported in the table below.

|  | Control A | Control B | Test | | | |
|---|---|---|---|---|---|---|
| Copolymer | none | ACP4a-4d | ACP 4a | ACP 4b | ACP 4c | ACP 4d |
| Packaging Saline | IPC-5E | PBS | IPC-5E | | | |
| Contact angle (°) | 104 | 103-110 | 64 | 63 | 76 | 66 |
| WBUT (s) | 1 | 1-2 | 2 | 1 | 1 | 3 |
| Lubricity | 3.5 | 3 | 2 | 2 | 2.5 | 3 |
| Low pH CLAN | Fail | Fail | Pass | Pass | Pass | Pass |

Example 9

Preparation of Lenses.

Silicone hydrogel contact lenses with a PAA coating thereon are prepared according to the procedures (the lens formulation, molds, cast-molding conditions, lens extraction, PAA coating solution, PAA coating procedures, etc.) described in Example 19 of U.S. patent application publication No. 2012/0026458 A1 (herein incorporated by reference in its entirety).

Preparation of AZM/APMA/DMA Containing Copolymer.

In a 500 mL glass reaction kettle, 1.0 gram of aminopropylmethacrylamide (APMA), 2.5 grams of AZM prepared in Example 2, 6.47 grams of N,N'-dimethylacrylamide (DMA), and 3.00 mL of Irgacure 2959 solution (1% in water) are dissolved in 187.0 grams of 33.75 mM citrate buffer (pH 4). A lid is put onto the reaction kettle that contains at least 4 ground glass joints. One used for a glass stir shaft, one for a thermocouple, one for a nitrogen inlet, and one for sampling access. The solution is sparged with nitrogen for 20 minutes at about 200 mL/min. The nitrogen flow rate is reduced to about 150 mL/min. The stir speed is set to 150 rpm. The reaction kettle is put into a Rayonet UV reactor with RPR-3500 UV bulbs. Four UV bulbs are turned on for about 1 hour at an intensity of about 2.0 mW/cm$^2$. After about one hour, the solution is vacuum filtered through qualitative filter paper. The copolymer solution is then purified using 50 kDa dialysis membranes against water for 24 hours using a water flow rate of about 40 mL/min. The solids content is determined and diluted to 2% if necessary.

Preparation of IPC Saline Using AZM/APMA/DMA Co-Polymer.

IPC 9A is prepared by making a 0.5% w/w solution of the AZM/APMA/DMA copolymer prepared above. A 2% copolymer solution is diluted by the PBS concentrate in Example 5 (50% w/w) and water (25% w/w) to get the final concentration of 0.5 w/w % Poly(AAm-co-AA)(90/10) partial sodium salt (~90% solid content, poly(AAm-co-AA) 90/10, Mw 200,000) is purchased from Polysciences, Inc. and used as received. IPC 9B is prepared by dissolving about 0.1% w/w of poly(AAm-co-AA)(90/10) and about 0.5% w/w of the AZM/APMA/DMA copolymer. IPC 9C is prepared by dissolving about 0.3% w/w of poly(AAm-co-AA)(90/10) and about 0.5% w/w of the AZM/APMA/DMA copolymer. Both IPC 9B and 9C are adjusted to pH 7.2-7.4 by adding about 0.044 w/w % NaH$_2$PO$_4$.H$_2$O, about 0.388 w/w/% Na$_2$HPO$_4$.2H$_2$O and about 0.79 w/w % NaCl. After that, IPC 9B and 9C are pre-heated for 10 hours at 70° C. During this heat pretreatment, poly(AAm-co-AA) and AZM copolymer are partially reacted to each other (i.e., not consuming all azetidinium groups of the copolymer) to form a water-soluble and thermally-crosslinkable hydrophilic polymeric material containing azetidinium groups within the branched polymer network in the IPC 9B and 9C. After the heat pre-treatment, the IPC is filtered using a 0.22 micron PES membrane filter.

Application of the Cross-Linked Coating.

PAA coated lenses are packaged in polypropylene shells (one lens per shell) containing 0.65 ml of either IPC 9A, 9B or 9C. Blisters are sealed and autoclaved for 45 min at 121° C.

Characterization of the Lenses.

Tests are done on the lenses to determine the efficacy of the coating salines. As can be seen, the copolymer of AZM/APMA/DMA itself is not capable of providing good lubricity on the lenses but addition of poly (AAm-co-AA) improves the lubricity tremendously.

| Packaging Saline | IPC 9A | IPC 9B | IPC 9C |
|---|---|---|---|
| WBUT (s) | 9 | 8-10 | 10-11 |
| Lubricity | 4 | 0.5 | 0 |
| Low pH CLAN | Pass | Pass | Pass |
| Bead Testing | Pass (2) | Pass (2) | Pass (0) |

Example 10

Preparation of Lenses.

Silicone hydrogel contact lenses with a PAA coating thereon are prepared according to the procedures (the lens formulation, molds, cast-molding conditions, lens extraction, PAA coating solution, PAA coating procedures, etc.) described in Example 19 of U.S. patent application publication No. 2012/0026458 A1 (herein incorporated by reference in its entirety).

Preparation of Copolymers of Methacrylic Acid, Acrylic Acid, and AZM.

In a 500 mL glass reaction kettle, methacrylic acid (MAA), acrylic acid (AA), 158 grams of 25% sodium citrate dehydrate solution in water, AZM prepared in Example 2, and 2.65 mL of Irgacure 2959 solution (1% in water) are added. The pH is adjusted to 5.5 using 5N NaOH. Water is added up to 265 grams. A lid is put onto the reaction kettle that contains at least 4 ground glass joints. One used for a glass stir shaft, one for a thermocouple, one for a nitrogen inlet, and one for sampling access. The solution is sparged with nitrogen for 20 minutes at about 200 mL/min. The nitrogen flow rate is reduced to about 150 mL/min. The stir speed is set to 150 rpm. The reaction kettle is put into a Rayonet UV reactor with RPR-3500 UV bulbs. Two UV bulbs are turned on for about 1 hour at an intensity of about 2.0 mW/cm$^2$. After about one hour, the solution is vacuum filtered through qualitative filter paper. The copolymer solution is then purified by ultrafiltration using a 10 kDa membranes until the solution conductivity reaches less than 10 uS/cm. The solids content is determined and diluted to 0.8% if necessary. Various copolymers are prepared with the ratios given in the table below.

|  | 10A | 10B | 10C | 10D | 10E |
|---|---|---|---|---|---|
| MAA (g) | 26.5 | 21.2 | 18.5 | 23.85 | 23.85 |
| AA (g) | — | 5.3 | 5.3 | — | 1.33 |
| AZM (g) | — | — | 2.65 g | 2.65 | 1.33 |
| 5N NaOH (mL) | 39 | 43 | 37.5 | 35 | 41 |
| DI water (g) | 38.9 | 37.4 | 40.4 | 40.7 | 38.0 |

Example 11

Preparation of Lenses.

Silicone hydrogel contact lenses are prepared by cast-molding according the procedures (the lens formulation, molds, cast-molding conditions, etc.) described in Example 19 of U.S. patent application publication No. 2012/0026458 A1 (herein incorporated by reference in its entirety).

PMAA Copolymer Coating Solution.

Polymethacrylic acid (PMAA) copolymer coating solutions are prepared from PMAA copolymers prepared in Example 10 to have the following composition: PMAA copolymer (0.011% w/w) which is one of PMAA 10A to 10E prepared in Example 10; 1-propanol (86.63% w/w); water (9.63% w/w); and formic acid (3.74% w/w).

PMAA Copolymer Coated Lenses.

Cast-molded contact lenses obtained as above are extracted and coated by dipping in the following series of baths: DI water bath for about 56 seconds; 3 methyl ethyl ketone (MEK) baths for about 22, 78, 226 second respectively; one DI water bath for about 56 seconds; one bath of PMAA copolymer coating solution (prepared above) for about 100 seconds; one bath of a water/1-propanol 50%/50% mixture for about 56 seconds; one bath of water for about 56 seconds; one bath of phosphate buffered saline for about 56 seconds; and one DI water bath for about 56 seconds. The lenses are immediately tested for acid group content by TBO Assay as described in Example 1. The data are shown below.

|  | 10A | 10B | 10C | 10D | 10E |
|---|---|---|---|---|---|
| TBO Assay (nanomoles/lens) | 12.4 +/− 1.0 | 29.9 +/− 1.1 | 5.0 +/− 2.6 | 4.9 +/− 1.5 | 7.1 +/− 1.0 |

Example 12

13.0 g methacrylic acid and 1.2 mg mercaptoethanol are dissolved in 243.0 g water and the pH adjusted to 3.0 by adding aqueous sodium hydroxide solution (33%). The solution is purged for 1 hour gently with nitrogen under stirring in a round flask. The solution is heated to 90° C. after degassing. 3.6 mg 2,2'-Azobis[2-methyl-N-(2-hydroxyethyl)propionamide] (VA-086, Wako) are separately dissolved in 5 mL water, purged with nitrogen for 1 hour, filled into a syringe and added to the synthesis solution to start the polymerization. The synthesis is carried out for 20 hours under stirring at 90° C. After the polymerization the pH of the synthesis solution is adjusted to pH=3 by adding sulfuric acid and the PMAA is purified by aqueous ultrafiltration with 10 kDa cellulose membranes (12× solvent exchange). PMAA is finally dried by freeze drying.

Example 13

15.0 g methacrylic acid and 3.4 mg mercaptoethanol are dissolved in 285.0 g water and the pH adjusted to 3.5 by adding aqueous sodium hydroxide solution (33%). The solution is purged gently for 1 hour with nitrogen under stirring in a round flask. The solution is heated to 50° C. after degassing. 9.1 mg 2,2'-Azobis[2-(2-imidazolin-2-yl)propane] (VA-061, Wako) are separately dissolved in 5 mL water, gently purged with nitrogen for 1 hour, filled into a syringe and added to the synthesis solution to start the polymerization. The synthesis is carried out for 20 hours under stirring at 50° C. After the polymerization the pH of the synthesis solution is adjusted to pH=3 by adding sulfuric acid and the PMAA is purified by aqueous ultrafiltration with 10 kDa cellulose membranes (12× solvent exchange). PMAA is finally dried by freeze drying.

Example 14

Various lenses (Purevision® from Bausch & Lamb; ACUVUE® 2® from Johnson & Johnson; SiHy lenses with FS PMAA/IPC-5A coating thereon as prepared in Example 7; SiHy lenses with 40×PMAA/IPC-5A coating thereon as prepared in Example 7; SiHy lenses with ACP-4e/IPC-5A coating thereon as prepared according to the procedures described in Example 8 and by using ACP-4e prepared in Example 4 as the prime coating and IPC saline IPC-5A prepared in Example 5 in forming the crosslinked coating) are tested for polyhexamethylene biguanide (PHMB) uptake and release according to the procedures described in Example 1. The results of the tests are shown in FIG. 1. The PHMB uptake is least for lenses having an ACP prime coating.

What is claimed is:

1. A method for producing coated silicone hydrogel contact lenses each having a crosslinked hydrophilic coating, comprising steps of:
   (a) obtaining a silicone hydrogel contact lens;
   (b) applying a prime coating of an anchoring polymer onto the silicone hydrogel contact lens, wherein the anchoring polymer is
      (i) a first azetidinium-containing copolymer which comprises 1) first azetidinium-containing monomeric units, 2) monomeric units selected from the group consisting of first carboxyl-containing monomeric units, hydrophobic monomeric units, and combination thereof, and 3) optionally first amino-containing monomeric units,
      wherein the first azetidinium-containing monomeric units are derived from at least one first azetidinium-containing vinylic monomer of formula (2)

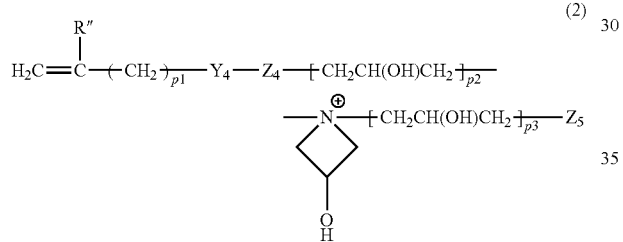

in which:
R" is hydrogen or methyl;
p1, p2, and p3 independent of one another are zero or 1;
$Y_4$ is a linkage selected from the group consisting of a direct bond, —O—, —NR'—, —C(O)—NR'—, —NR'—C(O)—, —O—C(O)—NH—, —NH—C(O)—O—, —NR'—C(O)—NH—, —NH—C(O)—NR'—, —C(O)—O—, —O—C(O)—, R' is hydrogen, a $C_1$-$C_{20}$ unsubstituted or substituted, linear or branched alkyl group;
$Z_4$, is a direct bond, a $C_1$-$C_{20}$ unsubstituted or substituted, linear or branched alkylene divalent radical optionally containing therein one or more linkages of —O—, —NR'—, and —C(O)—, a $C_1$-$C_7$ alkyleneoxy $C_1$-$C_7$ alkylene divalent radical, or a divalent radical of —(CH(R")CH$_2$O)$_{r1}$—CH(R")CH$_2$— in which R" is as defined above and r1 is an integer of 1 to 20; and
$Z_5$ is a $C_1$-$C_{20}$ unsubstituted or substituted, linear or branched alkyl group, —(CH$_2$)$_{r2}$—O—(CH$_2$CH$_2$O)$_{r1}$—$Z_6$ in which r1 is as defined above, r2 is zero or an integer of 1 to 7, and $Z_6$ is a $C_1$-$C_5$ alkyl,
wherein the first carboxyl-containing monomeric units are derived from at least one first carboxyl-containing vinylic monomer,
wherein the hydrophobic monomeric units are derived from at least one hydrophobic vinylic monomer,
wherein the first amino-containing monomeric units are derived from at least one first amino-containing vinylic monomer, and/or
      (ii) a homopolymer or copolymer of a carboxyl-containing vinylic monomer; and
   (c) heating the silicone hydrogel contact lens in an aqueous solution in the presence of a water-soluble, thermally-crosslinkable hydrophilic polymeric material comprising reactive functional groups selected from the group consisting of azetidinium groups, carboxyl groups, amino groups, thiol groups, and combinations thereof, at a temperature from about 40° C. to about 140° C. for a period of time sufficient to induce intermolecular and intramolecular crosslinking reaction between one azetidinium group and one amino or carboxyl group, thereby forming a durable non-silicone hydrogel coating on the silicone hydrogel contact lens,
provided that at least one of the anchoring polymer and the thermally-crosslinkable hydrophilic polymeric material comprises azetidinium groups.

2. The method of claim 1, wherein the thermally-crosslinkable hydrophilic polymeric material is:
   (i) a second azetidinium-containing copolymer which comprises second azetidinium-containing monomeric units, reactive monomeric units which are second carboxyl-containing monomeric units and/or second amino-containing monomeric units, and non-reactive hydrophilic monomeric units;
   (ii) a reaction product of the second azetidinium-containing copolymer with at least one hydrophilicity-enhancing agent having at least one reactive functional group selected from the group consisting of amino group, carboxyl group, thiol group, and combinations thereof;
   (iii) a reaction product of polyaminoamide-epichlorohydrin with at least one hydrophilicity-enhancing agent having at least one reactive functional group selected from the group consisting of amino group, carboxyl group, thiol group, and combinations thereof;
   (iv) a water-soluble hydrophilic polymer having at least one reactive functional group selected from the group consisting of amino group, carboxyl group, thiol group, and combinations thereof; or
   (v) combinations thereof,
wherein the second azetidinium-containing monomeric units are derived from at least one second azetidinium-containing vinylic monomer of formula (2)

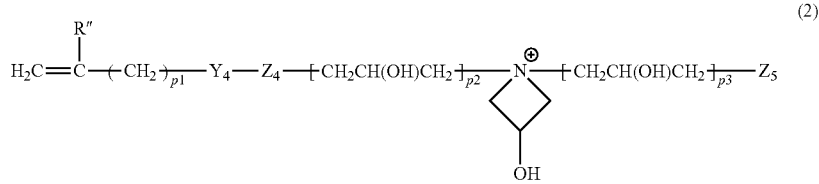

in which:
R" is hydrogen or methyl;
p1, p2, and p3 independent of one another are zero or 1;
$Y_4$ is a linkage selected from the group consisting of a direct bond, —O—, —NR'—, —C(O)—NR'—, —NR'—C(O)—, —O—C(O)—NH—, —NH—C(O)—O—, —NR'—C(O)—NH—, —NH—C(O)—NR'—, —C(O)—O—, —O—C(O)—, R' is hydrogen, a $C_1$-$C_{20}$ unsubstituted or substituted, linear or branched alkyl group;
$Z_4$, is a direct bond, a $C_1$-$C_{20}$ unsubstituted or substituted, linear or branched alkylene divalent radical optionally containing therein one or more linkages of —O—, —NR'—, and —C(O)—, a $C_1$-$C_7$ alkyleneoxy $C_1$-$C_7$ alkylene divalent radical, or a divalent radical of —(CH(R")CH$_2$O)$_{r1}$—CH(R")CH$_2$— in which R" is as defined above and r1 is an integer of 1 to 20; and
$Z_5$ is a $C_1$-$C_{20}$ unsubstituted or substituted, linear or branched alkyl group, —(CH$_2$)$_{r2}$—O—(CH$_2$CH$_2$O)$_{r1}$—$Z_6$ in which r1 is as defined above, r2 is zero or an integer of 1 to 7, and $Z_6$ is a $C_1$-$C_5$ alkyl,
wherein the second carboxyl-containing monomeric units are derived from at least one second carboxyl-containing vinylic monomer,
wherein the second amino-containing monomeric units are derived from at least one second amino-containing vinylic monomer,
wherein the non-reactive hydrophilic monomeric units are derived from at least one hydrophilic vinylic monomer selected from the group consisting of (meth)acrylamide, N,N-dimethyl (meth)acrylamide, N-vinylpyrrolidone, N,N,-dimethylaminoethyl (meth)acrylate, N,N-dimethylaminopropyl (meth)acrylamide, glycerol methacrylate, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, hydroxypropyl (meth)acrylate, $C_1$-$C_4$-alkoxy polyethylene glycol (meth)acrylate having a weight average molecular weight of up to 1500 Daltons, N-vinyl formamide, N-vinyl acetamide, N-vinyl isopropylamide, N-vinyl-N-methyl acetamide, allyl alcohol, vinyl alcohol which is the hydrolyzed form of vinyl acetate in the azetidinium-containing copolymer, a phosphorylcholine-containing vinylic monomer, erythritol (meth)acrylate, arabitol (meth)acrylate, mannitol (meth)acrylate, ducitol (meth)acrylate, fucitol (meth)acrylate, iditol (meth)acrylate, innositol (meth)acrylate, xylitol (meth)acrylate, sorbitol (meth)acrylate, glucose (meth)acrylate, fructose (meth)acrylate, galactose (meth)acrylate, and combinations thereof.

3. The method of claim 2, wherein the second azetidinium-containing copolymer comprises at least about 50% by moles of non-reactive hydrophilic monomeric units.

4. The method of claim 3, wherein the anchoring polymer is: polyacrylic acid; polymethacrylic acid; polyethylacrylic acid, polypropylacrylic acid; a copolymer of at least two vinylic monomers selected from the group consisting of acrylic acid, methacrylic acid, ethylacrylic acid, and propylacrylic acid; polymaleic acid; a copolymer of maleic acid and one or more vinylic monomers; a copolymer composed of from about 0.05% to about 20% by moles of the first azetidinium-containing vinylic monomer and of from about 80% to about 99.95% by moles of one or more carboxyl-containing vinylic monomers selected from the group consisting of acrylic acid, methacrylic acid, ethylacrylic acid, propylacrylic acid, and combination thereof; or a combination thereof.

5. The method of claim 3, wherein the anchoring polymer is: polymethacrylic acid; polyethylacrylic acid, a copolymer of methacrylic acid and ethylacrylic acid; polymaleic acid; a copolymer composed of from about 0.1% to about 15% by moles of the first azetidinium-containing vinylic monomer and of from about 80% to about 99.95% by moles of one or more carboxyl-containing vinylic monomers selected from the group consisting of methacrylic acid, ethylacrylic acid, and combination thereof; or a combination thereof.

6. The method of claim 3, wherein the anchoring polymer is the first azetidinium-containing copolymer which is composed of from about 0.1% to about 15% by moles of the first azetidinium-containing vinylic monomer and of from about 80% to about 99.95% by moles of one or more carboxyl-containing vinylic monomers selected from the group consisting of methacrylic acid, ethylacrylic acid, and combination thereof.

7. The method of claim 3, wherein the step of heating is performed by autoclaving the silicone hydrogel contact lens immersed in a packaging solution in a sealed lens package at a temperature of from about 118° C. to about 125° C. for approximately 20-90 minutes.

8. The method of claim 7, wherein the packaging solution comprises from about 0.01% to about 2% by weight of the thermally-crosslinkable hydrophilic polymeric material.

9. A method for producing silicone hydrogel contact lenses each having a crosslinked hydrophilic coating, comprising steps of:
(a) obtaining a silicone hydrogel contact lens by polymerization in a mold of a lens-forming composition comprising a first azetidinium-containing vinylic monomer and/or a first azetidinium-containing copolymer comprising first azetidinium-containing monomeric units derived from at least one second azetidinium-containing vinylic monomer and hydrophobic monomeric units derived from at least one hydrophobic vinylic monomer,
wherein the first and second azetidinium-containing vinylic monomers independent of each other are represented by formula (2)

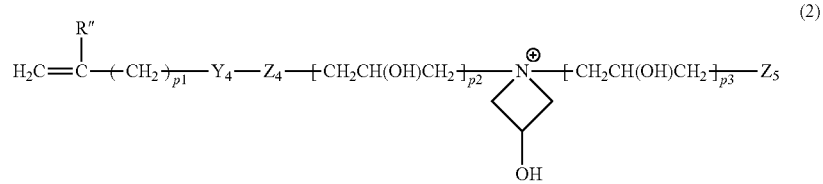

(2)

in which:
  R" is hydrogen or methyl;
  p1, p2, and p3 independent of one another are zero or 1;
  $Y_4$ is a linkage selected from the group consisting of a direct bond, —O—, —NR'—, —C(O)—NR'—, —NR'—C(O)—, —O—C(O)—NH—, (iv) a water-soluble hydrophilic polymer having at least one reactive functional group selected from the group consisting of amino group, carboxyl group, thiol group, and combinations thereof; or
  (v) combinations thereof,
  wherein the second azetidinium-containing monomeric units are derived from at least one third azetidinium-containing vinylic monomer of formula (2)

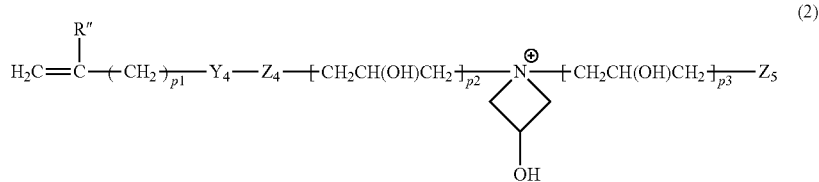

(2)

in which:
  R" is hydrogen or methyl;
  p1, p2, and p3 independent of one another are zero or 1;
  $Y_4$ is a linkage selected from the group consisting of a direct bond, —O—, —NR'—, —C(O)—NR'—, —NR'—C(O)—, —O—C(O)—NH—, —NH—C(O)—O—, —NR'—C(O)—NH—, —NH—C(O)—NR'—, —C(O)—O—, —O—C(O)—, R' is hydrogen, a $C_1$-$C_{20}$ unsubstituted or substituted, linear or branched alkyl group;

—NH—C(O)—O—, —NR'—C(O)—NH—, —NH—C(O)—NR'—, —C(O)—O—, —O—C(O)—, R' is hydrogen, a $C_1$-$C_{20}$ unsubstituted or substituted, linear or branched alkyl group;

$Z_4$, is a direct bond, a $C_1$-$C_{20}$ unsubstituted or substituted, linear or branched alkylene divalent radical optionally containing therein one or more linkages of —O—, —NR'—, and —C(O)—, a $C_1$-$C_7$ alkyleneoxy $C_1$-$C_7$ alkylene divalent radical, or a divalent radical of —(CH(R")CH$_2$O)$_{r1}$—CH(R")CH$_2$— in which R" is as defined above and r1 is an integer of 1 to 20; and $Z_5$ is a $C_1$-$C_{20}$ unsubstituted or substituted, linear or branched alkyl group, —(CH$_2$)$_{r2}$—O—(CH$_2$CH$_2$O)$_{r1}$—$Z_6$ in which r1 is as defined above, r2 is zero or an integer of 1 to 7, and $Z_6$ is a $C_1$-$C_5$ alkyl;

(b) heating the obtained silicone hydrogel contact lens in an aqueous solution in the presence of a water-soluble, thermally-crosslinkable hydrophilic polymeric material comprising reactive functional groups selected from the group consisting of azetidinium groups, carboxyl groups, amino groups, thiol groups, and combinations thereof, at a temperature from about 40° C. to about 140° C. for a period of time sufficient to induce intermolecular and intramolecular crosslinking reactions between one azetidinium group and one amino or carboxyl group, thereby forming a durable non-silicone hydrogel coating on the silicone hydrogel contact lens.

10. The method of claim 9, wherein the thermally-crosslinkable hydrophilic polymeric material is:
  (i) a second azetidinium-containing copolymer which comprises second azetidinium-containing monomeric units, reactive monomeric units which are first carboxyl-containing monomeric units and/or first amino-containing monomeric units, and non-reactive hydrophilic monomeric units;
  (ii) a reaction product of the second azetidinium-containing copolymer with at least one hydrophilicity-enhancing agent having at least one reactive functional group selected from the group consisting of amino group, carboxyl group, thiol group, and combinations thereof;
  (iii) a reaction product of polyaminoamide-epichlorohydrin with at least one hydrophilicity-enhancing agent having at least one reactive functional group selected from the group consisting of amino group, carboxyl group, thiol group, and combinations thereof;

$Z_4$, is a direct bond, a $C_1$-$C_{20}$ unsubstituted or substituted, linear or branched alkylene divalent radical optionally containing therein one or more linkages of —O—, —NR'—, and —C(O)—, a $C_1$-$C_7$ alkyleneoxy $C_1$-$C_7$ alkylene divalent radical, or a divalent radical of —(CH(R")CH$_2$O)$_{r1}$—CH(R")CH$_2$— in which R" is as defined above and r1 is an integer of 1 to 20; and $Z_5$ is a $C_1$-$C_{20}$ unsubstituted or substituted, linear or branched alkyl group, —(CH$_2$)$_{r2}$—O—(CH$_2$CH$_2$O)$_{r1}$—$Z_6$ in which r1 is as defined above, r2 is zero or an integer of 1 to 7, and $Z_6$ is a $C_1$—C alkyl, wherein the first carboxyl-containing monomeric units are derived from at least one first carboxyl-containing vinylic monomer, wherein the first amino-containing monomeric units are derived from at least one first amino-containing vinylic monomer, wherein the non-reactive hydrophilic monomeric units are derived from at least one hydrophilic vinylic monomer selected from the group consisting of (meth)acrylamide, N,N-dimethyl (meth)acrylamide, N-vinylpyrrolidone, N,N,-dimethylaminoethyl (meth)acrylate, N,N-dimethylaminopropyl (meth)acrylamide, glycerol methacrylate, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, hydroxypropyl (meth)acrylate, $C_1$-$C_4$-alkoxy polyethylene glycol (meth)acrylate having a weight average molecular weight of up to 1500 Daltons, N-vinyl formamide, N-vinyl acetamide, N-vinyl isopropylamide, N-vinyl-N-methyl acetamide, allyl alcohol, vinyl alcohol which is the hydrolyzed form of vinyl acetate in the azetidinium-containing copolymer, a phosphorylcholine-containing vinylic monomer, erythritol (meth)acrylate, arabitol (meth)acrylate, mannitol (meth)acrylate, ducitol (meth)acrylate, fucitol (meth)acrylate, iditol (meth)acrylate, innositol (meth)acrylate, xylitol (meth)acrylate, sorbitol (meth)acrylate, glucose (meth)acrylate, fructose (meth)acrylate, galactose (meth)acrylate, and combinations thereof.

11. The method of claim 10, wherein the second azetidinium-containing copolymer comprises at least about 50% by moles of non-reactive hydrophilic monomeric units.

12. The method of claim 11, wherein the step of heating is performed by autoclaving the silicone hydrogel contact lens immersed in a packaging solution in a sealed lens package at a temperature of from about 118° C. to about 125° C. for approximately 20-90 minutes.

13. The method of claim 12, further comprising a step of applying a prime coating of an anchoring polymer onto the silicone hydrogel contact lens.

14. The method of claim 13, wherein the anchoring polymer is: polyacrylic acid; polymethacrylic acid; polyethylacrylic acid, polypropylacrylic acid; a copolymer of at least two vinylic monomers selected from the group consisting of acrylic acid, methacrylic acid, ethylacrylic acid, and propylacrylic acid; polymaleic acid; a copolymer of maleic acid and one or more vinylic monomers; a copolymer composed of from about 0.05% to about 20% by moles of the first azetidinium-containing vinylic monomer and of from about 80% to about 99.95% by moles of one or more carboxyl-containing vinylic monomers selected from the group consisting of acrylic acid, methacrylic acid, ethylacrylic acid, propylacrylic acid, and combination thereof; or a combination thereof.

15. The method of claim 13, wherein the anchoring polymer is: polymethacrylic acid; polyethylacrylic acid, a copolymer of methacrylic acid and ethylacrylic acid; polymaleic acid; a copolymer composed of from about 0.1% to about 15% by moles of the first azetidinium-containing vinylic monomer and of from about 80% to about 99.95% by moles of one or more carboxyl-containing vinylic monomers selected from the group consisting of methacrylic acid, ethylacrylic acid, and combination thereof; or a combination thereof.

16. The method of claim 13, wherein the anchoring polymer is a third azetidinium-containing copolymer which comprises:

third azetidinium-containing monomeric units derived from at least one fourth azetidinium-containing vinylic monomer of formula (2)

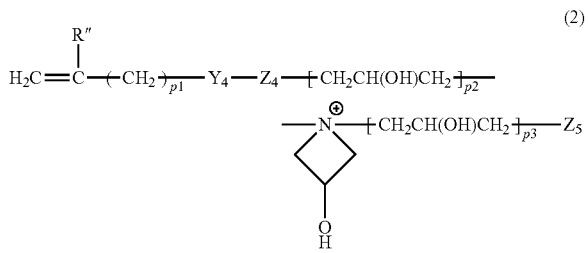

in which:
R″ is hydrogen or methyl;
p1, p2, and p3 independent of one another are zero or 1;
$Y_4$ is a linkage selected from the group consisting of a direct bond, —O—, —NR′—, —C(O)—NR′—, —NR′—C(O)—, —O—C(O)—NH—, —NH—C(O)—O—, —NR′—C(O)—NH—, —NH—C(O)—NR′—, —C(O)—O—, —O—C(O)—, R′ is hydrogen, a $C_1$-$C_{20}$ unsubstituted or substituted, linear or branched alkyl group;
$Z_4$, is a direct bond, a $C_1$-$C_{20}$ unsubstituted or substituted, linear or branched alkylene divalent radical optionally containing therein one or more linkages of —O—, —NR′—, and —C(O)—, a $C_1$-$C_7$ alkyleneoxy $C_1$-$C_7$ alkylene divalent radical, or a divalent radical of —(CH(R″)CH$_2$O)$_{r1}$—CH(R″)CH$_2$— in which R″ is as defined above and r1 is an integer of 1 to 20; and
$Z_5$ is a $C_1$-$C_{20}$ unsubstituted or substituted, linear or branched alkyl group, —(CH$_2$)$_{r2}$—O—(CH$_2$CH$_2$O)$_{r1}$—$Z_6$ in which r1 is as defined above, r2 is zero or an integer of 1 to 7, and $Z_6$ is a $C_1$-$C_5$ alkyl; and
monomeric units derived from at least one vinylic monomer selected from the group consisting of a carboxyl-containing vinylic monomer, an amino-containing vinylic monomer, a hydrophobic vinylic monomer, and combination thereof.

* * * * *